United States Patent
Rudakov

(10) Patent No.: US 11,224,438 B2
(45) Date of Patent: Jan. 18, 2022

(54) TREATMENT OF INCOMPETENT VESSELS

(71) Applicant: ArtVentive Medical Group, Inc., San Marcos, CA (US)

(72) Inventor: Leon Rudakov, San Marcos, CA (US)

(73) Assignee: ArtVentive Medical Group, Inc., San Marcos, CA (US)

( * ) Notice: Subject to any disclaimer, the term of this patent is extended or adjusted under 35 U.S.C. 154(b) by 374 days.

(21) Appl. No.: 16/518,933

(22) Filed: Jul. 22, 2019

(65) Prior Publication Data

US 2019/0343530 A1 Nov. 14, 2019

Related U.S. Application Data

(63) Continuation of application No. 14/697,547, filed on Apr. 27, 2015, now Pat. No. 10,363,043.
(Continued)

(51) Int. Cl.
*A61B 17/12* (2006.01)
*A61B 17/00* (2006.01)
(Continued)

(52) U.S. Cl.
CPC .... *A61B 17/1215* (2013.01); *A61B 17/12031* (2013.01); *A61B 17/12145* (2013.01);
(Continued)

(58) Field of Classification Search
CPC ........ A61B 17/12145; A61B 17/12172; A61B 17/122; A61B 17/1227; A61B 17/12022;
(Continued)

(56) References Cited

U.S. PATENT DOCUMENTS 3,805,767 A   4/1974   Erb
3,868,956 A   3/1975   Alfidi et al.
(Continued)

FOREIGN PATENT DOCUMENTS

CN   2527227   12/2002
EP   1166721   1/2002
(Continued)

OTHER PUBLICATIONS

U.S. Appl. No. 11/825,956, filed Jul. 9, 2007, now U.S. Pat. No. 8,328,840.
(Continued)

*Primary Examiner* — Wade Miles
*Assistant Examiner* — Mikail A Mannan
(74) *Attorney, Agent, or Firm* — Nathan S. Smith; Sujohn Das; Morgan, Lewis & Bockius LLP

(57) ABSTRACT

A method of implanting an occlusive device in a perforator vessel may include introducing a needle through skin of a patient, and advancing the needle into a perforator vessel, the perforator vessel extending between a superficial vein and a deep vein. The method may further include distally advancing a delivery component from within the needle until a distal end of the delivery component extends into the deep vein and releasing a distal portion of the occlusive device into the deep vein. The needle may then be proximally withdrawn from the perforator vessel such that the device is exposed within the vessel, and the proximal portion of the device may be released into the superficial vein such that the device blocks flow through the vessel.

20 Claims, 16 Drawing Sheets

Related U.S. Application Data

(60) Provisional application No. 61/987,446, filed on May 1, 2014.

(51) Int. Cl.
*A61B 17/34* (2006.01)
*A61B 17/42* (2006.01)

(52) U.S. Cl.
CPC ... *A61B 17/12104* (2013.01); *A61B 17/12109* (2013.01); *A61B 2017/00004* (2013.01); *A61B 2017/00597* (2013.01); *A61B 2017/1205* (2013.01); *A61B 2017/12127* (2013.01); *A61B 2017/3413* (2013.01); *A61B 2017/4233* (2013.01)

(58) Field of Classification Search
CPC .......... A61B 17/12046; A61B 17/1204; A61B 17/12104; A61B 17/12109; A61B 2017/1205; A61B 2017/12127; A61F 2/86; A61F 2/88; A61F 2/885; A61F 2/89; A61F 2/90; A61F 2002/826; A61F 2/24; A61F 2/2409; A61F 2/2418
See application file for complete search history.

(56) References Cited

U.S. PATENT DOCUMENTS

| | | |
|---|---|---|
| 3,918,431 A | 11/1975 | Sinnreich |
| 4,013,063 A | 3/1977 | Bucalo |
| 4,245,623 A | 1/1981 | Erb |
| 4,553,545 A | 11/1985 | Maass et al. |
| 4,649,922 A | 3/1987 | Wiktor |
| 4,682,592 A | 7/1987 | Thorsgard |
| 4,705,517 A | 11/1987 | DiPisa, Jr. |
| 4,706,671 A | 11/1987 | Weinrib |
| 4,733,665 A | 3/1988 | Palmaz |
| 4,739,762 A | 4/1988 | Palmaz |
| 4,768,507 A | 9/1988 | Fischell et al. |
| 4,776,337 A | 10/1988 | Palmaz |
| 4,800,882 A | 1/1989 | Gianturco |
| 4,827,946 A | 5/1989 | Kaali et al. |
| 4,913,141 A | 4/1990 | Hillstead |
| 4,969,890 A | 11/1990 | Sugita et al. |
| 5,037,427 A | 8/1991 | Harada et al. |
| 5,065,751 A | 11/1991 | Wolf |
| 5,089,005 A | 2/1992 | Harada |
| 5,102,417 A | 4/1992 | Palmaz |
| 5,147,370 A | 9/1992 | McNamara et al. |
| 5,234,437 A | 8/1993 | Sepetka |
| 5,242,451 A | 9/1993 | Harada et al. |
| 5,242,452 A | 9/1993 | Inoue |
| 5,304,198 A | 4/1994 | Samson |
| 5,324,306 A | 6/1994 | Makower et al. |
| 5,334,210 A | 8/1994 | Gianturco |
| 5,342,387 A | 8/1994 | Summers |
| 5,372,600 A | 12/1994 | Beyar et al. |
| 5,417,708 A | 5/1995 | Hall et al. |
| 5,474,089 A | 12/1995 | Waynant |
| 5,476,505 A | 12/1995 | Limon |
| 5,499,995 A | 3/1996 | Teirstein |
| 5,536,274 A | 7/1996 | Neuss |
| 5,562,641 A | 10/1996 | Flomenblit et al. |
| 5,562,698 A | 10/1996 | Parker |
| 5,607,445 A | 3/1997 | Summers |
| 5,656,036 A | 8/1997 | Palmaz |
| 5,674,287 A | 10/1997 | Slepian et al. |
| 5,693,083 A | 12/1997 | Baker et al. |
| 5,725,552 A | 3/1998 | Kotula et al. |
| 5,733,329 A | 3/1998 | Wallace et al. |
| 5,772,668 A | 6/1998 | Summers et al. |
| 5,782,860 A | 7/1998 | Epstein et al. |
| 5,797,952 A | 8/1998 | Klein |
| 5,797,953 A | 8/1998 | Tekulve |
| 5,830,222 A | 11/1998 | Makower |
| 5,842,621 A | 12/1998 | Gschwind |
| 5,868,782 A | 2/1999 | Frantzen |
| 5,902,266 A | 5/1999 | Leone et al. |
| 5,922,009 A | 7/1999 | Epstein et al. |
| 5,925,063 A | 7/1999 | Khosravi |
| 5,925,074 A | 7/1999 | Gingras et al. |
| 5,928,260 A | 7/1999 | Chin et al. |
| 5,944,738 A | 8/1999 | Amplatz et al. |
| 5,954,766 A | 9/1999 | Zadno-Azizi et al. |
| 5,957,929 A | 9/1999 | Brenneman |
| 5,979,446 A | 11/1999 | Loy |
| 6,010,517 A | 1/2000 | Baccaro |
| 6,019,779 A | 2/2000 | Thorud et al. |
| 6,024,765 A | 2/2000 | Wallace et al. |
| 6,056,770 A | 5/2000 | Epstein et al. |
| 6,059,825 A | 5/2000 | Hobbs et al. |
| 6,083,257 A | 7/2000 | Taylor et al. |
| 6,117,157 A | 9/2000 | Tekulve |
| 6,123,715 A | 9/2000 | Amplatz |
| 6,168,622 B1 | 1/2001 | Mazzocchi |
| 6,190,353 B1 | 2/2001 | Makower et al. |
| 6,210,338 B1 | 4/2001 | Afremov et al. |
| 6,214,042 B1 | 4/2001 | Jacobsen et al. |
| 6,241,678 B1 | 6/2001 | Afremov et al. |
| 6,241,758 B1 | 6/2001 | Cox |
| 6,245,090 B1 | 6/2001 | Gilson et al. |
| 6,248,122 B1 | 6/2001 | Klumb et al. |
| 6,258,119 B1 | 7/2001 | Hussein et al. |
| 6,283,983 B1 | 9/2001 | Makower et al. |
| 6,334,864 B1 | 1/2002 | Amplatz et al. |
| 6,346,118 B1 | 2/2002 | Baker et al. |
| 6,361,558 B1 | 3/2002 | Hieshima et al. |
| 6,368,339 B1 | 4/2002 | Amplatz |
| 6,371,953 B1 | 4/2002 | Beyar et al. |
| 6,371,979 B1 | 4/2002 | Beyar et al. |
| 6,402,760 B1 | 6/2002 | Fedida |
| 6,402,772 B1 | 6/2002 | Amplatz et al. |
| 6,432,116 B1 | 8/2002 | Callister et al. |
| 6,432,127 B1 | 8/2002 | Kim et al. |
| 6,447,531 B1 | 9/2002 | Amplatz |
| 6,451,025 B1 | 9/2002 | Jervis |
| 6,454,780 B1 | 9/2002 | Wallace |
| 6,464,712 B1 | 10/2002 | Epstein et al. |
| 6,468,301 B1 | 10/2002 | Amplatz et al. |
| 6,485,524 B2 | 11/2002 | Strecker |
| 6,506,204 B2 | 1/2003 | Mazzocchi |
| 6,514,285 B1 | 2/2003 | Pinchasik |
| 6,533,805 B1 | 3/2003 | Jervis |
| 6,550,480 B2 | 4/2003 | Feldman et al. |
| 6,554,849 B1 | 4/2003 | Jones et al. |
| 6,562,064 B1 | 5/2003 | deBeer |
| 6,572,643 B1 | 6/2003 | Gharibadeh |
| 6,579,303 B2 | 6/2003 | Amplatz |
| 6,585,760 B1 | 7/2003 | Fogarty |
| 6,599,308 B2 | 7/2003 | Amplatz |
| 6,602,271 B2 | 8/2003 | Adams et al. |
| 6,613,074 B1 | 9/2003 | Mitelberg |
| 6,616,675 B1 | 9/2003 | Evard et al. |
| 6,623,518 B2 | 9/2003 | Thompson et al. |
| 6,629,981 B2 | 10/2003 | Bui et al. |
| 6,638,243 B2 | 10/2003 | Kupiecki |
| 6,638,257 B2 | 10/2003 | Amplatz |
| 6,638,293 B1 | 10/2003 | Makower et al. |
| 6,645,237 B2 | 11/2003 | Klumb et al. |
| 6,656,207 B2 | 12/2003 | Epstein et al. |
| 6,660,020 B2 | 12/2003 | Wallace et al. |
| 6,660,032 B2 | 12/2003 | Klumb et al. |
| 6,663,666 B1 | 12/2003 | Quiachon et al. |
| 6,682,546 B2 | 1/2004 | Amplatz |
| 6,689,148 B2 | 2/2004 | Sawhney et al. |
| 6,702,846 B2 | 3/2004 | Mikus et al. |
| 6,719,781 B1 | 4/2004 | Kim |
| 6,790,218 B2 | 9/2004 | Jayaraman |
| 6,849,081 B2 | 2/2005 | Sepetka et al. |
| 6,872,211 B2 | 3/2005 | White et al. |
| 6,890,341 B2 | 5/2005 | Dieck et al. |
| 6,899,730 B1 | 5/2005 | Rivelli, Jr. |
| 6,936,058 B2 | 8/2005 | Forde et al. |

(56) References Cited

U.S. PATENT DOCUMENTS

| | | |
|---|---|---|
| 6,974,473 B2 | 12/2005 | Barclay et al. |
| 6,984,244 B2 | 1/2006 | Perez et al. |
| 7,001,409 B2 | 2/2006 | Amplatz |
| 7,011,643 B2 | 3/2006 | Villafana et al. |
| 7,011,671 B2 | 3/2006 | Welch |
| 7,144,408 B2 | 12/2006 | Keegan et al. |
| 7,152,605 B2 | 12/2006 | Khairkhahan et al. |
| 7,220,270 B2 | 5/2007 | Sawhney et al. |
| 7,270,668 B2 | 9/2007 | Andreas et al. |
| 7,276,077 B2 | 10/2007 | Zadno-Azizi et al. |
| 7,294,146 B2 | 11/2007 | Chew et al. |
| 7,303,571 B2 | 12/2007 | Makower et al. |
| 7,387,641 B2 | 6/2008 | Schmitt |
| 7,396,362 B2 | 7/2008 | Jervis |
| 7,398,780 B2 | 7/2008 | Callister et al. |
| 7,458,986 B2 | 12/2008 | Schmitt |
| 7,476,232 B2 | 1/2009 | Deal |
| 7,582,100 B2 | 9/2009 | Johnson et al. |
| 7,597,704 B2 | 10/2009 | Frazier et al. |
| 7,604,649 B2 | 10/2009 | McGuckin, Jr. et al. |
| 7,632,291 B2 | 12/2009 | Stephens et al. |
| 7,647,930 B2 | 1/2010 | Ginn |
| 7,651,521 B2 | 1/2010 | Ton et al. |
| 7,666,204 B2 | 2/2010 | Thornton et al. |
| 7,682,673 B2 | 3/2010 | Houston et al. |
| 7,691,124 B2 | 4/2010 | Balgobin |
| 7,699,056 B2 | 4/2010 | Tran et al. |
| 7,740,616 B2 | 6/2010 | Smith et al. |
| 7,771,463 B2 | 8/2010 | Ton et al. |
| 7,785,343 B2 | 8/2010 | Johnson et al. |
| 7,785,631 B2 | 8/2010 | Roser et al. |
| 7,789,860 B2 | 9/2010 | Brady et al. |
| 7,789,892 B2 | 9/2010 | Johnson et al. |
| 7,803,177 B2 | 9/2010 | Hartley et al. |
| 7,854,747 B2 | 12/2010 | Johnson et al. |
| 7,955,343 B2 | 6/2011 | Makower et al. |
| 7,967,837 B2 | 6/2011 | Vale |
| 7,985,250 B2 | 7/2011 | Kaufmann et al. |
| 7,992,565 B2 | 8/2011 | McGuckin, Jr. et al. |
| 8,016,870 B2 | 9/2011 | Chew et al. |
| 8,016,880 B2 | 9/2011 | Cook et al. |
| 8,043,357 B2 | 10/2011 | Hartley |
| 8,100,958 B2 | 1/2012 | Fischer et al. |
| 8,110,267 B2 | 2/2012 | Houston et al. |
| 8,114,114 B2 | 2/2012 | Belson |
| 8,118,852 B2 | 2/2012 | Melsheimer |
| 8,142,456 B2 | 3/2012 | Rosqueta et al. |
| 8,162,970 B2 | 4/2012 | Gilson et al. |
| 8,226,679 B2 | 7/2012 | Johnson et al. |
| 8,226,704 B2 | 7/2012 | Caro et al. |
| 8,298,257 B2 | 10/2012 | Sepetka et al. |
| 8,308,754 B2 | 11/2012 | Belson |
| 8,323,305 B2 | 12/2012 | Epstein et al. |
| 8,323,350 B2 | 12/2012 | Nissl |
| 8,328,840 B2 | 12/2012 | Gailloud et al. |
| 8,333,783 B2 | 12/2012 | Braun et al. |
| 8,333,796 B2 | 12/2012 | Tompkins et al. |
| 8,343,167 B2 | 1/2013 | Henson |
| 8,348,994 B2 | 1/2013 | Leopold et al. |
| 8,382,771 B2 | 2/2013 | Gellman et al. |
| 8,382,821 B2 | 2/2013 | Richter |
| 8,398,700 B2 | 3/2013 | Leopold et al. |
| 8,425,549 B2 | 4/2013 | Lenker et al. |
| 8,430,904 B2 | 4/2013 | Belson |
| 8,663,301 B2 | 3/2014 | Riina et al. |
| 2001/0000798 A1 | 5/2001 | Denardo |
| 2001/0007946 A1 | 7/2001 | Lenker et al. |
| 2001/0031981 A1 | 10/2001 | Evans et al. |
| 2001/0037146 A1 | 11/2001 | Lau et al. |
| 2001/0044648 A1 | 11/2001 | Wolinsky et al. |
| 2001/0046518 A1 | 11/2001 | Sawhney |
| 2002/0007206 A1 | 1/2002 | Bui et al. |
| 2002/0091439 A1 | 7/2002 | Baker et al. |
| 2002/0099437 A1 | 7/2002 | Anson et al. |
| 2002/0107565 A1 | 8/2002 | Greenhalgh |
| 2002/0123765 A1 | 9/2002 | Sepetka et al. |
| 2002/0128707 A1 | 9/2002 | Kavteladze et al. |
| 2002/0143362 A1 | 10/2002 | Macoviak et al. |
| 2002/0177855 A1 | 11/2002 | Greene et al. |
| 2002/0198588 A1 | 12/2002 | Armstrong et al. |
| 2003/0114922 A1 | 6/2003 | Iwasaka et al. |
| 2003/0125798 A1 | 7/2003 | Martin |
| 2003/0130684 A1 | 7/2003 | Brady et al. |
| 2003/0153972 A1 | 8/2003 | Helmus |
| 2003/0163146 A1 | 8/2003 | Epstein et al. |
| 2003/0171801 A1 | 9/2003 | Bates |
| 2003/0187474 A1 | 10/2003 | Keegan et al. |
| 2003/0187495 A1 | 10/2003 | Cully et al. |
| 2003/0216679 A1 | 11/2003 | Wolf et al. |
| 2003/0229366 A1 | 12/2003 | Reggie et al. |
| 2004/0010282 A1 | 1/2004 | Kusleika |
| 2004/0029994 A1 | 2/2004 | Cheng et al. |
| 2004/0044360 A1 | 3/2004 | Lowe |
| 2004/0055606 A1 | 3/2004 | Hendricksen et al. |
| 2004/0073252 A1 | 4/2004 | Goldberg et al. |
| 2004/0147869 A1 | 7/2004 | Wolf et al. |
| 2004/0153118 A1 | 8/2004 | Clubb et al. |
| 2004/0158308 A1 | 8/2004 | Hogendijk et al. |
| 2004/0193141 A1 | 9/2004 | Leopold et al. |
| 2004/0220663 A1 | 11/2004 | Rivelli |
| 2004/0225286 A1 | 11/2004 | Elliott |
| 2004/0243219 A1 | 12/2004 | Fischer et al. |
| 2004/0249342 A1 | 12/2004 | Khosravi et al. |
| 2004/0254517 A1 | 12/2004 | Quiroz-Mercado et al. |
| 2004/0260384 A1 | 12/2004 | Allen |
| 2005/0027305 A1 | 2/2005 | Shiu et al. |
| 2005/0033409 A1 | 2/2005 | Burke et al. |
| 2005/0043759 A1 | 2/2005 | Chanduszko |
| 2005/0055079 A1 | 3/2005 | Duran |
| 2005/0055082 A1 | 3/2005 | Ben Muvhar et al. |
| 2005/0113902 A1 | 5/2005 | Geiser et al. |
| 2005/0137681 A1 | 6/2005 | Shoemaker et al. |
| 2005/0165442 A1 | 7/2005 | Thinnes et al. |
| 2005/0192616 A1 | 9/2005 | Callister et al. |
| 2005/0209675 A1 | 9/2005 | Ton et al. |
| 2005/0288684 A1 | 12/2005 | Aronson et al. |
| 2006/0009798 A1 | 1/2006 | Callister et al. |
| 2006/0052822 A1* | 3/2006 | Mirizzi ............ A61B 17/1219 606/214 |
| 2006/0111771 A1 | 5/2006 | Ton et al. |
| 2006/0119714 A1 | 6/2006 | Tamura et al. |
| 2006/0149359 A1 | 7/2006 | Richter et al. |
| 2006/0162731 A1 | 7/2006 | Wondka et al. |
| 2006/0178727 A1 | 8/2006 | Richter |
| 2006/0184089 A1 | 8/2006 | Makower et al. |
| 2006/0200191 A1 | 9/2006 | Zadno-Azizi |
| 2006/0241675 A1 | 10/2006 | Johnson et al. |
| 2006/0241690 A1 | 10/2006 | Amplatz et al. |
| 2007/0038178 A1 | 2/2007 | Kusleika |
| 2007/0043419 A1 | 2/2007 | Nikolchev et al. |
| 2007/0060946 A1 | 3/2007 | Keegan et al. |
| 2007/0088388 A1 | 4/2007 | Opolski et al. |
| 2007/0112381 A1 | 5/2007 | Figulla et al. |
| 2007/0118209 A1 | 5/2007 | Strecker |
| 2007/0129753 A1 | 6/2007 | Quinn et al. |
| 2007/0135826 A1 | 6/2007 | Zaver et al. |
| 2007/0150045 A1 | 6/2007 | Ferrera |
| 2007/0156224 A1 | 7/2007 | Cioanta et al. |
| 2007/0163601 A1 | 7/2007 | Pollock et al. |
| 2007/0168018 A1 | 7/2007 | Amplatz et al. |
| 2007/0168019 A1 | 7/2007 | Amplatz et al. |
| 2007/0203503 A1 | 8/2007 | Salahieh et al. |
| 2007/0221230 A1 | 9/2007 | Thompson et al. |
| 2007/0233186 A1 | 10/2007 | Meng |
| 2007/0239191 A1 | 10/2007 | Ramzipoor |
| 2007/0247680 A1 | 10/2007 | Nakane et al. |
| 2007/0265656 A1 | 11/2007 | Amplatz et al. |
| 2007/0265658 A1 | 11/2007 | Nelson et al. |
| 2008/0017201 A1 | 1/2008 | Sawhney |
| 2008/0045996 A1 | 2/2008 | Makower et al. |
| 2008/0046092 A1 | 2/2008 | Davis et al. |
| 2008/0086214 A1 | 4/2008 | Hardin et al. |
| 2008/0103522 A1 | 5/2008 | Steingisser et al. |
| 2008/0132906 A1 | 6/2008 | Rasmussen |

(56) References Cited

U.S. PATENT DOCUMENTS

| | | |
|---|---|---|
| 2008/0178890 A1 | 7/2008 | Townsend et al. |
| 2008/0200945 A1 | 8/2008 | Amplatz et al. |
| 2008/0215087 A1 | 9/2008 | Pavcnik et al. |
| 2008/0221600 A1 | 9/2008 | Dieck et al. |
| 2008/0221666 A1 | 9/2008 | Licata et al. |
| 2008/0269719 A1 | 10/2008 | Balgobin et al. |
| 2008/0302368 A1 | 12/2008 | McGuckin, Jr. et al. |
| 2009/0005847 A1 | 1/2009 | Adams |
| 2009/0018562 A1 | 1/2009 | Amplatz et al. |
| 2009/0018636 A1 | 1/2009 | Gailloud et al. |
| 2009/0025820 A1 | 1/2009 | Adams |
| 2009/0030497 A1 | 1/2009 | Metcalf et al. |
| 2009/0043330 A1 | 2/2009 | To |
| 2009/0062841 A1* | 3/2009 | Amplatz .......... A61B 17/12022 606/200 |
| 2009/0078270 A1 | 3/2009 | Meier et al. |
| 2009/0082803 A1 | 3/2009 | Adams et al. |
| 2009/0099647 A1 | 4/2009 | Glimsdale et al. |
| 2009/0112251 A1 | 4/2009 | Qian et al. |
| 2009/0131959 A1 | 5/2009 | Rolland |
| 2009/0132020 A1 | 5/2009 | Watson |
| 2009/0138078 A1 | 5/2009 | Paul, Jr. et al. |
| 2009/0157053 A1 | 6/2009 | Davis et al. |
| 2009/0171386 A1 | 7/2009 | Amplatz et al. |
| 2009/0178682 A1 | 7/2009 | Tal et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0216185 A1 | 8/2009 | Gregorich et al. |
| 2009/0240326 A1 | 9/2009 | Wilson et al. |
| 2009/0276029 A1 | 11/2009 | Caro et al. |
| 2009/0276039 A1 | 11/2009 | Meretei |
| 2009/0277455 A1 | 11/2009 | Lee-Sepsick et al. |
| 2009/0281610 A1 | 11/2009 | Parker |
| 2010/0006105 A1 | 1/2010 | Carter et al. |
| 2010/0030321 A1 | 2/2010 | Mach |
| 2010/0049307 A1 | 2/2010 | Ren |
| 2010/0057194 A1 | 3/2010 | Ryan |
| 2010/0063578 A1 | 3/2010 | Ren et al. |
| 2010/0063582 A1 | 3/2010 | Rudakov |
| 2010/0089406 A1 | 4/2010 | Kachiguina |
| 2010/0094395 A1 | 4/2010 | Kellett |
| 2010/0106235 A1 | 4/2010 | Kariniemi et al. |
| 2010/0114307 A1 | 5/2010 | Agnew et al. |
| 2010/0121370 A1 | 5/2010 | Kariniemi |
| 2010/0174269 A1 | 7/2010 | Tompkins et al. |
| 2010/0198328 A1 | 8/2010 | Hartley et al. |
| 2010/0223046 A1 | 9/2010 | Bucchieri et al. |
| 2010/0223048 A1 | 9/2010 | Lauder |
| 2010/0249691 A1 | 9/2010 | Van Der Mooren et al. |
| 2010/0256661 A1* | 10/2010 | Brandeis .......... A61B 17/12172 606/159 |
| 2010/0268201 A1 | 10/2010 | Tieu et al. |
| 2010/0268260 A1 | 10/2010 | Riina et al. |
| 2010/0294282 A1 | 11/2010 | Chu et al. |
| 2010/0312268 A1 | 12/2010 | Belson |
| 2010/0318178 A1 | 12/2010 | Rapaport et al. |
| 2010/0324585 A1 | 12/2010 | Miles et al. |
| 2010/0324586 A1 | 12/2010 | Miles et al. |
| 2010/0324587 A1 | 12/2010 | Miles et al. |
| 2010/0324588 A1 | 12/2010 | Miles et al. |
| 2011/0029067 A1 | 2/2011 | McGuckin, Jr. et al. |
| 2011/0040371 A1 | 2/2011 | Hanssen et al. |
| 2011/0092997 A1 | 4/2011 | Kang |
| 2011/0124958 A1 | 5/2011 | Nelson |
| 2011/0125132 A1 | 5/2011 | Krolik et al. |
| 2011/0202087 A1 | 8/2011 | Vale |
| 2011/0202129 A1 | 8/2011 | Fofsell |
| 2011/0218479 A1 | 9/2011 | Rottenberg et al. |
| 2011/0264132 A1 | 10/2011 | Strauss et al. |
| 2011/0264195 A1 | 10/2011 | Griswold |
| 2011/0282343 A1 | 11/2011 | Kunis |
| 2011/0301630 A1 | 12/2011 | Hendriksen et al. |
| 2011/0313506 A1 | 12/2011 | Ray et al. |
| 2011/0319906 A1 | 12/2011 | Rudakov et al. |
| 2012/0010556 A1 | 1/2012 | Faul et al. |
| 2012/0022572 A1 | 1/2012 | Braun et al. |
| 2012/0059458 A1 | 3/2012 | Buchbinder |
| 2012/0071918 A1 | 3/2012 | Amin |
| 2012/0083822 A1 | 4/2012 | Anukhin et al. |
| 2012/0089216 A1 | 4/2012 | Rapaport et al. |
| 2012/0095489 A1 | 4/2012 | Rudakov et al. |
| 2012/0101510 A1 | 4/2012 | Lenker et al. |
| 2012/0116350 A1 | 5/2012 | Strauss et al. |
| 2012/0123511 A1 | 5/2012 | Brown |
| 2012/0123514 A1 | 5/2012 | Kunis |
| 2012/0143301 A1 | 6/2012 | Maslanka et al. |
| 2012/0172911 A1 | 7/2012 | Welch |
| 2012/0192872 A1 | 8/2012 | Rudakov et al. |
| 2012/0209310 A1 | 8/2012 | Chen et al. |
| 2012/0239077 A1 | 9/2012 | Zaver et al. |
| 2012/0245614 A1* | 9/2012 | Drasler .......... A61B 17/12109 606/191 |
| 2012/0245620 A1 | 9/2012 | Gilson et al. |
| 2012/0245668 A1 | 9/2012 | Kariniemi et al. |
| 2012/0259354 A1 | 10/2012 | Kellett |
| 2012/0277842 A1 | 11/2012 | Kunis |
| 2012/0289988 A1 | 11/2012 | Riina et al. |
| 2012/0289994 A1 | 11/2012 | Larson et al. |
| 2012/0296408 A1 | 11/2012 | Jones et al. |
| 2012/0316584 A1 | 12/2012 | Miles et al. |
| 2012/0330347 A1 | 12/2012 | Becking et al. |
| 2012/0330348 A1 | 12/2012 | Strauss et al. |
| 2013/0041404 A1 | 2/2013 | Amin |
| 2013/0053879 A1 | 2/2013 | Gailloud et al. |
| 2013/0102996 A1 | 4/2013 | Strauss |
| 2013/0103074 A1 | 4/2013 | Riina et al. |
| 2013/0109987 A1 | 5/2013 | Kunis et al. |
| 2013/0116774 A1 | 5/2013 | Strauss et al. |
| 2013/0123899 A1 | 5/2013 | Leopold et al. |
| 2013/0178889 A1 | 7/2013 | Miles et al. |
| 2013/0204282 A1 | 8/2013 | Nelson |
| 2013/0204311 A1 | 8/2013 | Kunis |
| 2013/0289714 A1 | 10/2013 | Strauss et al. |
| 2014/0128780 A1 | 5/2014 | Kennedy et al. |
| 2014/0207180 A1 | 7/2014 | Ferrera |
| 2014/0215792 A1 | 8/2014 | Leopold et al. |
| 2014/0222059 A1 | 8/2014 | Leopold et al. |
| 2014/0257369 A1 | 9/2014 | Leopold et al. |
| 2014/0277085 A1 | 9/2014 | Mirigian et al. |
| 2014/0371716 A1 | 12/2014 | Rudakov |
| 2014/0371777 A1 | 12/2014 | Rudakov et al. |
| 2014/0371778 A1 | 12/2014 | Rudakov et al. |
| 2015/0057700 A1 | 2/2015 | Chen et al. |
| 2015/0157329 A1 | 6/2015 | Rudakov et al. |
| 2015/0157333 A1 | 6/2015 | Leopold et al. |
| 2015/0223821 A1 | 8/2015 | Rudakov et al. |
| 2015/0290437 A1 | 10/2015 | Rudakov et al. |
| 2015/0342611 A1 | 12/2015 | Leopold et al. |

FOREIGN PATENT DOCUMENTS

| | | |
|---|---|---|
| EP | 1188413 | 3/2002 |
| EP | 1317908 | 6/2003 |
| EP | 1600110 | 11/2005 |
| EP | 1707233 | 10/2006 |
| EP | 1752112 | 2/2007 |
| EP | 1813196 | 8/2007 |
| EP | 1820436 | 8/2007 |
| EP | 1852073 | 11/2007 |
| EP | 2248471 | 11/2010 |
| EP | 2366362 | 9/2011 |
| EP | 2366363 | 9/2011 |
| EP | 2366364 | 9/2011 |
| EP | 2404580 | 1/2012 |
| EP | 2583636 | 4/2013 |
| GB | 2404860 | 2/2005 |
| GB | 2494820 | 3/2013 |
| JP | H 07-000405 | 1/1995 |
| JP | H 07-185011 | 7/1995 |
| JP | 2006-181015 | 7/2006 |
| JP | 2010-532180 | 10/2010 |
| JP | 2012-525859 | 10/2012 |

(56) References Cited

FOREIGN PATENT DOCUMENTS

| | | |
|---|---|---|
| WO | WO 83/00997 | 3/1983 |
| WO | WO 92/14408 | 9/1992 |
| WO | WO 94/000179 | 1/1994 |
| WO | WO 95/24158 | 9/1995 |
| WO | WO 95/25480 | 9/1995 |
| WO | WO 95/32018 | 11/1995 |
| WO | WO 96/18361 | 6/1996 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 97/31672 | 9/1997 |
| WO | WO 98/08456 | 3/1998 |
| WO | WO 98/31308 | 7/1998 |
| WO | WO 98/34546 | 8/1998 |
| WO | WO 98/46115 | 10/1998 |
| WO | WO 98/46119 | 10/1998 |
| WO | WO 99/12484 | 3/1999 |
| WO | WO 99/23976 | 5/1999 |
| WO | WO 99/25273 | 5/1999 |
| WO | WO 99/44542 | 9/1999 |
| WO | WO 99/48545 | 9/1999 |
| WO | WO 99/49793 | 10/1999 |
| WO | WO 99/49910 | 10/1999 |
| WO | WO 99/62430 | 12/1999 |
| WO | WO 00/09195 | 2/2000 |
| WO | WO 00/16847 | 3/2000 |
| WO | WO 00/27303 | 5/2000 |
| WO | WO 00/67671 | 11/2000 |
| WO | WO 01/032254 | 5/2001 |
| WO | WO 01/64112 | 9/2001 |
| WO | WO 01/080776 | 11/2001 |
| WO | WO 01/080777 | 11/2001 |
| WO | WO 01/89413 | 11/2001 |
| WO | WO 02/03889 | 1/2002 |
| WO | WO 03/001970 | 1/2003 |
| WO | WO 03/073961 | 9/2003 |
| WO | WO 03/073962 | 9/2003 |
| WO | WO 03/101518 | 12/2003 |
| WO | WO 2004/006804 | 1/2004 |
| WO | WO 2004/073557 | 9/2004 |
| WO | WO 2005/020786 | 3/2005 |
| WO | WO 2005/092241 | 10/2005 |
| WO | WO 2005/117755 | 12/2005 |
| WO | WO 2006/017470 | 2/2006 |
| WO | WO 2006/028943 | 3/2006 |
| WO | WO 2006/031602 | 3/2006 |
| WO | WO 2006/034153 | 3/2006 |
| WO | WO 2006/074163 | 7/2006 |
| WO | WO 2006/096342 | 9/2006 |
| WO | WO 2006/111801 | 10/2006 |
| WO | WO 2006/134354 | 12/2006 |
| WO | WO 2007/061927 | 5/2007 |
| WO | WO 2007/070544 | 6/2007 |
| WO | WO 2007/085373 | 8/2007 |
| WO | WO 2007/127351 | 11/2007 |
| WO | WO 2007/149844 | 12/2007 |
| WO | WO 2008/010197 | 1/2008 |
| WO | WO 2008/100790 | 8/2008 |
| WO | WO 2008/112501 | 9/2008 |
| WO | WO 2008/153653 | 12/2008 |
| WO | WO 2009/064618 | 5/2009 |
| WO | WO 2009/077845 | 6/2009 |
| WO | WO 2009/088905 | 7/2009 |
| WO | WO 2009/124288 | 10/2009 |
| WO | WO 2009/126747 | 10/2009 |
| WO | WO 2010/009019 | 1/2010 |
| WO | WO 2010/047644 | 4/2010 |
| WO | WO 2010/075565 | 7/2010 |
| WO | WO 2010/085344 | 7/2010 |
| WO | WO 2010/096717 | 8/2010 |
| WO | WO 2010/130617 | 11/2010 |
| WO | WO 2010/135352 | 11/2010 |
| WO | WO 2010/146581 | 12/2010 |
| WO | WO 2010/148246 | 12/2010 |
| WO | WO 2011/011581 | 1/2011 |
| WO | WO 2011/153304 | 12/2011 |
| WO | WO 2011/163157 | 12/2011 |
| WO | WO 2012/002944 | 1/2012 |
| WO | WO 2012/040380 | 3/2012 |
| WO | WO 2012/067724 | 5/2012 |
| WO | WO 2012/109367 | 8/2012 |
| WO | WO 2012/111137 | 8/2012 |
| WO | WO 2012/120490 | 9/2012 |
| WO | WO 2012/131672 | 10/2012 |
| WO | WO 2012/134761 | 10/2012 |
| WO | WO 2012/135859 | 10/2012 |
| WO | WO 2012/166804 | 12/2012 |
| WO | WO 2013/055703 | 4/2013 |
| WO | WO 2013/059511 | 4/2013 |
| WO | WO 2013/067299 | 5/2013 |

OTHER PUBLICATIONS

U.S. Appl. No. 12/826,593, filed Jun. 29, 2010, now U.S. Pub. 2011/0319906.
U.S. Appl. No. 12/906,993, filed Oct. 18, 2010, now U.S. Pub. 2012/0095489.
U.S. Appl. No. 13/367,338, filed Feb. 6, 2012, now U.S. Pub. 2012/0192872.
U.S. Appl. No. 13/670,345, filed Nov. 6, 2012, now U.S. Pub. 2013/0053879.
U.S. Appl. No. 13/828,974, filed Mar. 14, 2013, now U.S. Pub. 2014/0222059.
U.S. Appl. No. 14/044,794, filed Oct. 2, 2013, now U.S. Pub. 2014/0215792.
U.S. Appl. No. 14/101,171, filed Dec. 9, 2013, now U.S. Pub. 2014/0371716.
U.S. Appl. No. 14/281,797, filed May 19, 2014, now U.S. Pub. 2014/0257369.
U.S. Appl. No. 14/304,868, filed Jun. 13, 2014, now U.S. Pub. 2014/0371777.
U.S. Appl. No. 14/304,869, filed Jun. 13, 2014, now U.S. Pub. 2014/0371778.
U.S. Appl. No. 14/622,729, filed Feb. 13, 2015, now U.S. Pub. 2015/0157329.
U.S. Appl. No. 14/628,096, filed Feb. 20, 2015, now U.S. Pub. 2015/0157333.
U.S. Appl. No. 14/688,915, filed Apr. 16, 2015, now U.S. Pub. 2015/0223821.
U.S. Appl. No. 14/697,547, filed Apr. 27, 2015, now U.S. Pub. 2015/0313602.
U.S. Appl. No. 14/749,565, filed Jun. 24, 2015, now U.S. Pub. 2015/0290437.
Aydogan, Transcatheter Embolization Treatment of Coronary Arteriovenous Fistulas, Asian Cardiovascular & Thoracic Annals, 2003, pp. 63-67, vol. 11, No. 1.
Berguer et al., Cure by Combination of Operation and Detachable Intravascular Balloon, Ann. Surg. Jul. 1982, pp. 65-68, vol. 196, No. 1.
Cheng et al., Minimally Invasive Keyhole Approach for Removal of a Migratory Balloon Complicated by Endovascular Embolization of a Carotid-Cavernous Fistula, Minim. Invasive Neurosurgl, 2006, pp. 305-308, vol. 49.
Desouza et al., Embolization with detachable Balloons—Applications outside the head, Clinical Radiology, Apr. 21, 1992, pp. 170-175, vol. 46.
Ferro et al, Percutaneous Transcatheter Embolization of a Large Pulmonary Arteriovenous Fistula with an Amplatzer Vascular Plug, Cardovacs Intervent Radiol, 2007, pp. 328-331, vol. 30.
Hawkins et al., The Permeability of Detachable Latex Rubber Balloons—An In Vitro Study, Investigative Radiology, Dec. 1987, pp. 969-972, vol. 22.
Hirai et al., Emergency Balloon Embolization for Carotid Artery Rupture Secondary to Postoperative Infection, Cardiovasc Intervent Radiol, 1996, pp. 50-52, vol. 19.

(56) References Cited

OTHER PUBLICATIONS

Kadir et al., Therapeutic Embolization of the Kidney with Detachable Silicone Balloons, The Journal of Urology, Jan. 1983, pp. 11-13, vol. 129.
Kallmes et al., The Use of Hydrocoil for Parent Artery Occlusion, AJNR Am J Neuroradiol, Sep. 2004, pp. 1409-1410, vol. 25.
Kaufman, et al., Detachable Balloon-modified Reducing Stent to Treat Hepatic Insufficiency after Transjugular Intrahepatic Portosystemic Shunt Creation, J Vasc Interv Radiol., May 2003, pp. 635-638, vol. 14, No. 5.
Luo, Chao-Bao et al., Endovascular Treatment of the Carotid Artery Rupture with Massive Hemorrhage, J. Chin Med Assoc., Mar. 2003.
Makita, et al., Guide-Wire-directed Detachable Balloon: Clinical Application in Treatment of Varicoceles, Radiology, 1992, pp. 575-577, vol. 183.
Marshall et al., Treatment of Traumatic Renal Arteriovenous Fistulas by Detachable Silicone Balloon Embolization, The Journal of Urology, Aug. 1979, pp. 237-239, vol. 122.
Perala et al., Comparison of Early Deflation Rate of Detachable Latex and Silicone Balloons and Observations on Persistent Varicocele, J. Vasc. Interv. Radiol. Sep.-Oct. 1998, pp. 761-765, vol. 9, No. 5.
Pollak et al., Clinical Results of Transvenous Systemic Embolotherapy with a Neuroradiologic Detachable Balloon, Radiology, May 1994, pp. 477-482, vol. 191, No. 2.
Reidy et at., Transcatherer occlusion of coronary to bronchial anastomosis by detachable balloon combined with coronary angioplasty at same procedure, Brit Heart J. 1983, pp. 284-287, vol. 49.
Reidy et al., Transcatheter occlusion of a Blalock-Taussig shunt with a detachable balloon in a child, Bri Heart Journal, 1983, pp. 101-103, vol. 50.
Ross et al., The Vascular Plug: A New Device for Parent Artery Occlusion, AJNR Am J Neuroradiol, Feb. 2007, pp. 385-386, vol. 28.
Serbinenko, F.A., Balloon Catheterization and Occlusion of Major Cerebral Vessels, J. Neurosurg. Aug. 1974, pp. 125-145, vol. 41.
Tasar, et al., Intrahepatic arterioportal fistula and its treatment with detachable balloon and transcatheter embolization with coils and microspheres, Journal of Clinical Imaging, 2005, pp. 325-330, vol. 29.
Wehman, et al., Giant Cerebral Aneurysms: Endovascular Challenges, Neurosurgery, Nov. 2006, pp. S125-S138, vol. 59, No. 5.
White, et al., Occlusion of Varicoceles with Detachable Balloons, Radiology, May 1981, pp. 327-334, vol. 139.
Serbinenko, F.A., Occlusion by Balooning of Sacular Aneurysms of the Cerebral Arteries, Vopr, Neirokhir, Jul.-Aug. 1974, pp. 8-15, vol. 4.
Serebinko, F.A., Balloon Occlusion of Cavernous Portion of the Carotid Artery as a Method of Treating Carotid Cavity Anastomoses, Vopr. Neirokhir, Nov.-Dec. 1971, pp. 3-9, vol. 6.

\* cited by examiner

TREATMENT OF INCOMPETENT VESSELS

CROSS-REFERENCE TO RELATED APPLICATIONS

This application is a continuation of U.S. patent application Ser. No. 14/697,547, filed Apr. 27, 2015, which claims the priority benefit of U.S. Provisional Application No. 61/987,446, filed on May 1, 2014, the entirety of each of which is incorporated herein by reference.

FIELD

The subject technology relates generally to apparatuses and methods for blood vessel occlusion and vascular stenting.

BACKGROUND

Veins can become incompetent through the weakening of blood vessel walls or damage to or weakening of valves within the vein. Most frequently, veins carrying oxygen-depleted blood up the legs provide the most apparent visual evidence of the vessel wall or valve weakening, demonstrating that a portion of the veins have become incompetent. When the blood vessel walls weekend or the valves no longer serve their function of reducing or preventing backflow of blood, the vain can become enlarged, weak, and twisted. This condition is referred to as a varicose vein.

While the causes of varicose veins are varied and common, varicose veins can be treated using a variety of procedures.

SUMMARY

Treatment of varicose veins and other blood vessel problems can be achieved through some embodiments disclosed herein. Some embodiments herein relate to vessel occlusion by delivery of radially expandable implant frames that achieve immediate total occlusion of blood flow. Frame configurations, expected delivered and expanded dimensions, and a description of target anatomy of some embodiments is provided.

Aspects of implants and delivery devices that can be utilized in combination with the implants, systems, methods, and features disclosed herein are disclosed in: U.S. patent application Ser. No. 12/826,593, filed on Jun. 29, 2010; U.S. patent application Ser. No. 13/367,338, filed on Feb. 6, 2012; U.S. Patent Pub. No. US20120095489, published on Apr. 19, 2012; U.S. patent application Ser. No. 13/828,974, filed on Mar. 14, 2013, U.S. patent application Ser. No. 14/044,794, filed on Oct. 2, 2013; U.S. patent application Ser. No. 61/835,406, filed on Jun. 14, 2013; U.S. Patent App. No. 61/904,376, filed on Nov. 14, 2013; U.S. Patent App. No. 61/904,379, filed on Nov. 14, 2013; U.S. Patent App. No. 61/835,461, filed on Jun. 14, 2013; U.S. Patent App. No. 61/900,321, filed on Nov. 5, 2013; and U.S. patent application Ser. No. 14/101,171, filed on Dec. 9, 2013, the entireties of which are incorporated herein by reference.

Additionally, some embodiments provided herein relate to implantation in small blood vessels (veins or arteries), such as from about 3 mm to about 20 mm, from about 5 mm to about 15 mm, or from about 7 mm to about 11 mm. The target delivery profile can be from about 2 Fr to about 6 Fr, and in some embodiments, from about 3 Fr to about 5 Fr.

Further embodiments can provide vascular stenting for vessels that are from about 3 mm to about 16 mm, from about 5 mm to about 13 mm, and in some embodiments, from about 7 mm to about 11 mm. The target delivery profile can be from about 2 Fr to about 8 Fr, about 3 Fr to about 7 Fr, from about 4 Fr to about 6 Fr, or in some embodiments, about 5 Fr. Additionally, expansion of the implant can provide sufficient radial force against the inside wall of a vein. Some embodiments can comprise features or means configured to minimize backflow of blood or minimize venous insufficiency. For example, treatment applications for embodiments of the device can include ilio-femoral venous obstruction and chronic iliac venous outflow obstruction as a result of venous disease.

Further, some embodiments provided herein can be used to provide temporary or permanent occlusion of a vessel during and/or after treatment of a tumor by intravascular injection of fluids, chemotherapy drugs, liquid embolic agents, and/or other therapeutic agents delivered into the feeding vessels and/or into the tumor.

Some embodiments of the implants provided herein can be manufactured via several methods including shape-setting of drawn wire, chemical etching of a NiTi sheet of material, laser cutting of a tubular member, such as a material sheet or tubing, and/or electrical discharge machining (EDM) of a tubular member, such as a material sheet or tubing.

The implants disclosed herein can comprise flexible and/or shape memory materials such that they may be distorted from an expanded shape to a smaller diameter or straight shape to allow for delivery to a target location by way of a minimally invasive catheter-based approach.

In accordance with some embodiments, the implant can comprise a frame and a cover material. The cover material can comprise ePTFE tubing, film, and/or suture for attachment purposes. Additionally, the cover material may be fibrous, mesh-like, or impermeable in density.

The implant frame and/or implant cover can comprise a collagen coating or collagen treatment to improve anchoring of the implant in the target vessel. The collagen can be configured to promote cell adhesion to implant materials, thereby facilitating improved support for the implant and vessel structure while acting as an anti-migration feature for the implant.

The implant frame can comprise a straight or constant diameter, a tapering diameter, or sections of variable diameter extending over its length, which can facilitate anchoring within a vessel and optimal deployment function.

Some embodiments of the systems and devices disclosed herein address the unmet need for a device that can provide a fast, precise and reliable way to close a bodily lumen. The endoluminal occlusion system can include two major subsystems: a guide sheath assembly and an implant carrier assembly. The implant carrier assembly can include an implant device and a handle assembly. Embodiments of the present disclosure can also comprise various features disclosed in U.S. Pat. No. 8,328,840, issued on Dec. 11, 2012, the entirety of which is incorporated herein by reference.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

Figure 1A:
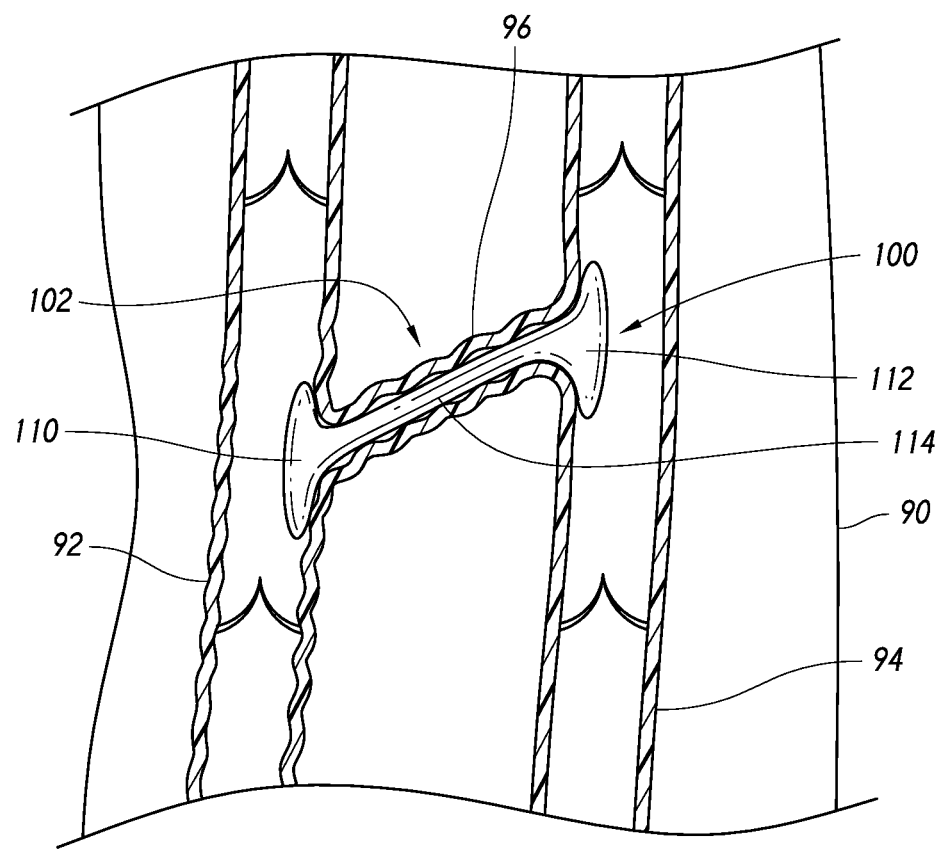
FIG. 1A is a perspective view of an occlusive device implanted in a perforator vessel, according to some embodiments.
Figure 1B:
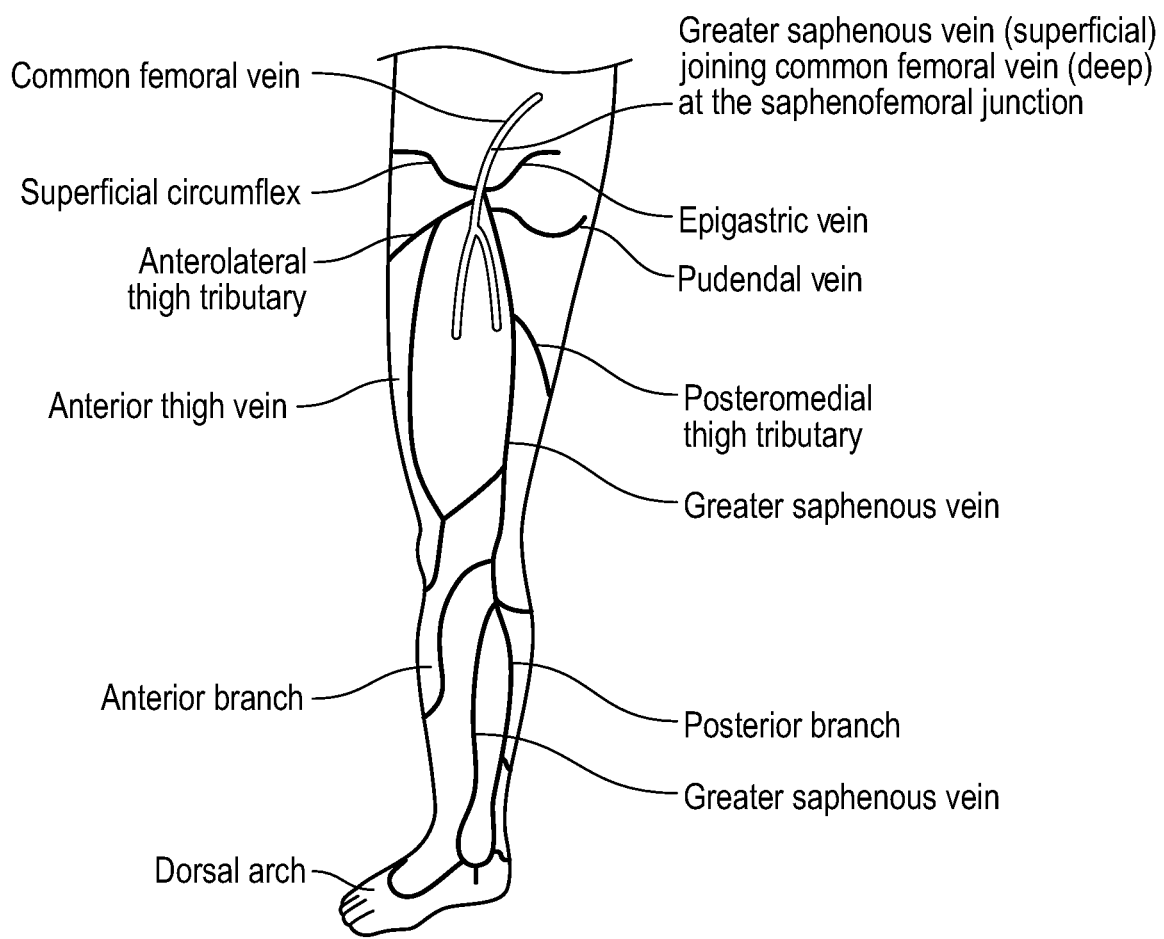
FIGS. 1B-1F are views of vasculature in a patient, which can represent target vessels that can be treated, according to some embodiments.
Figure 1C:
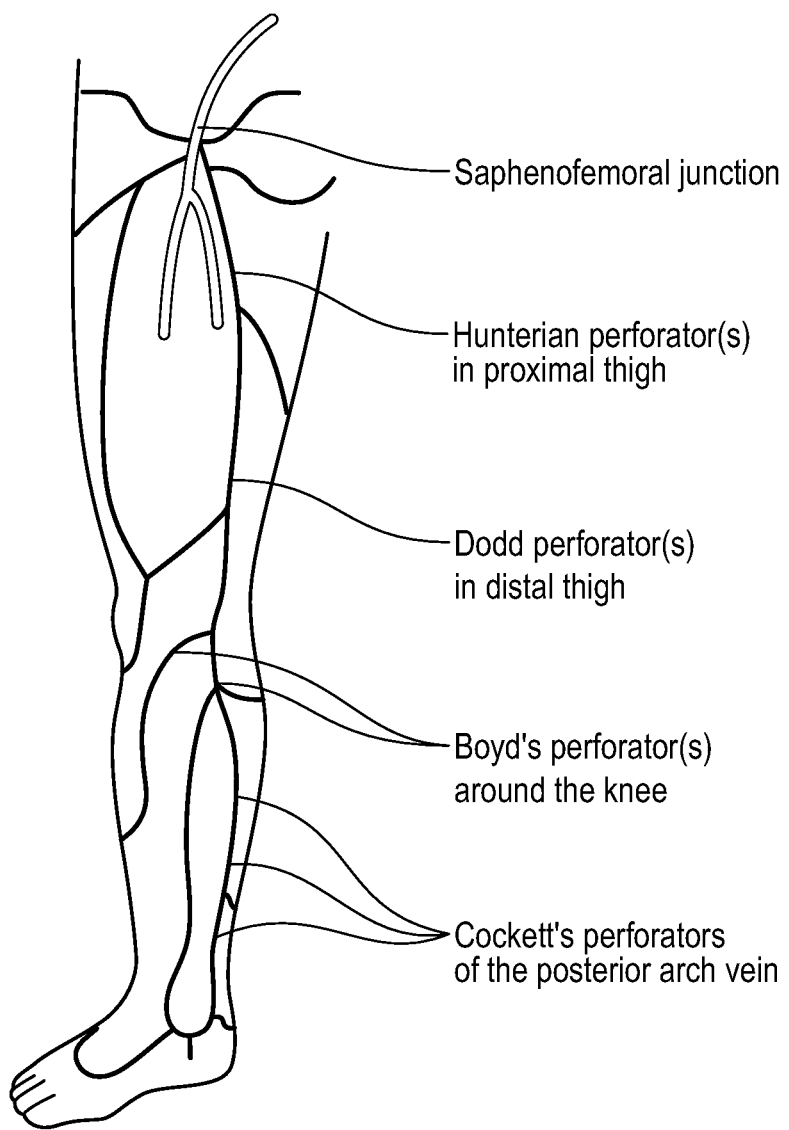
Figure 1D:
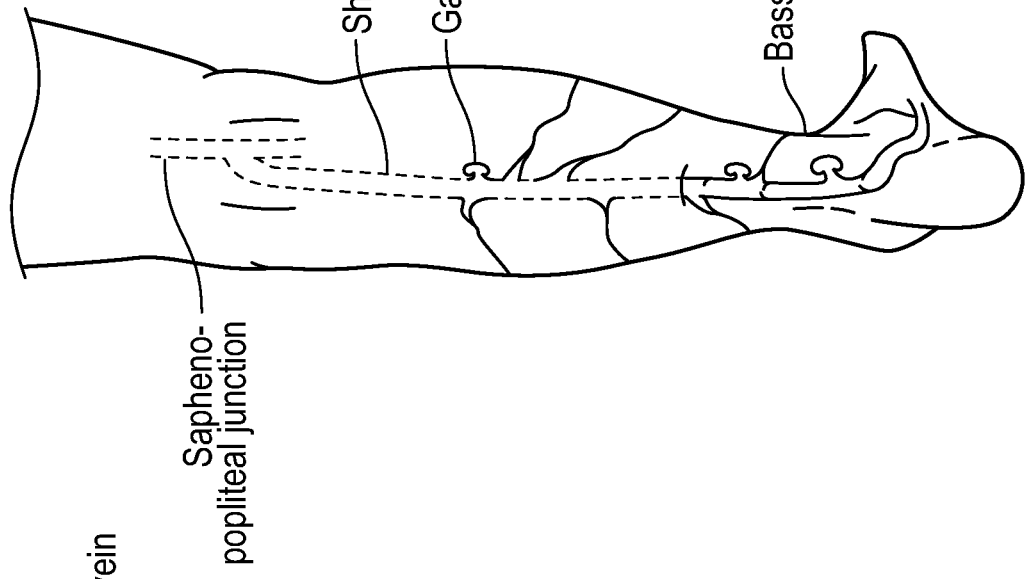
Figure 1D:
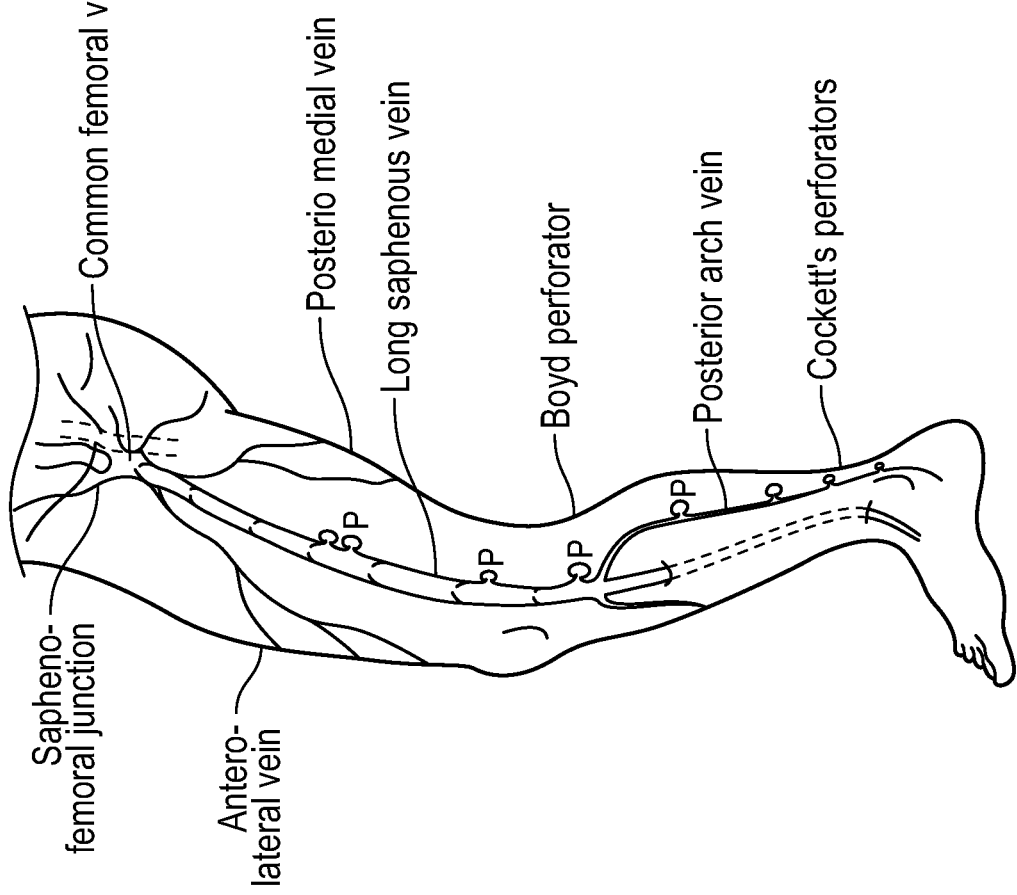
Figure 1E:
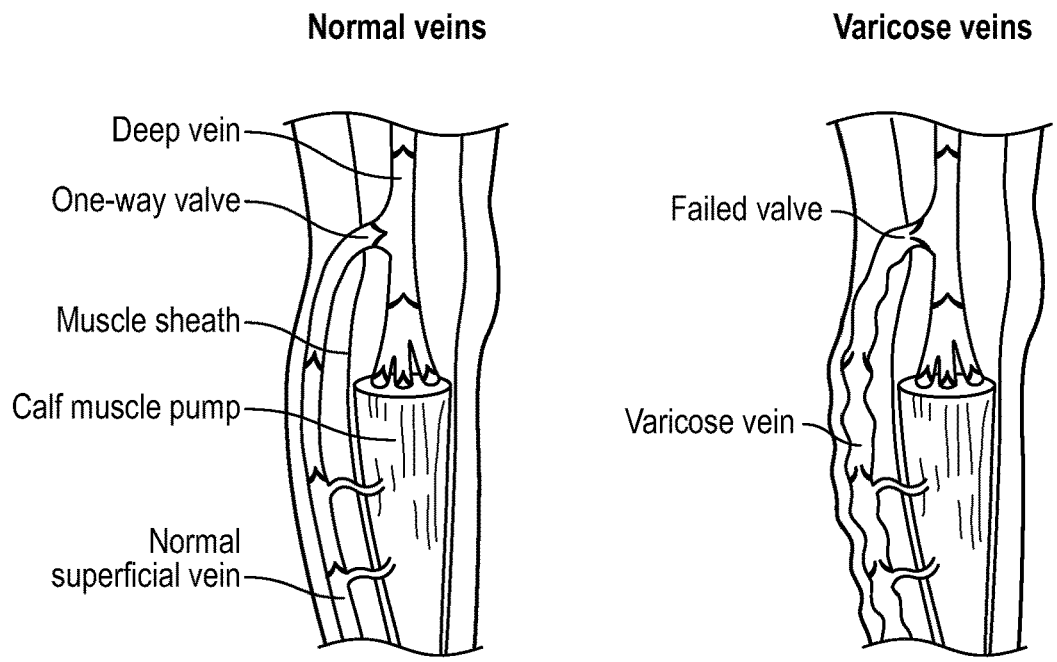
Figure 1F:
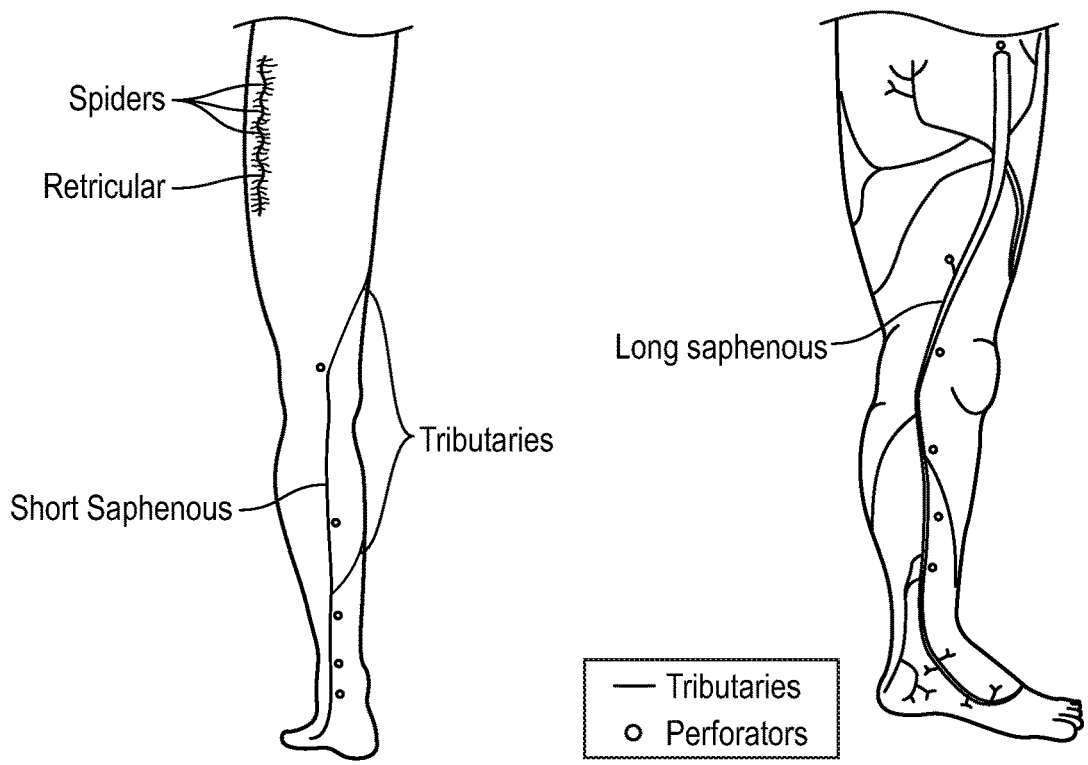

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

While the present description sets forth specific details of various embodiments, it will be appreciated that the description is illustrative only and should not be construed in any way as limiting. It is contemplated that although particular embodiments of the present inventions may be disclosed or shown in particular contexts, such embodiments can be used in a variety of endoluminal applications. Various applications of such embodiments and modifications thereto, which may occur to those who are skilled in the art, are also encompassed by the general concepts described herein.

The present disclosure provides various embodiments of an expandable device, such as a stent, and a catheter for supporting and delivering the stent, as well as methods of using the devices and catheters.

According to some embodiments, an occlusion system can quickly and reliably close vessels (veins or arteries) such as incompetent venous perforators and arterial venous fistulae. Some embodiments can be performed using minimally invasive techniques that allow a clinician to provide rapid and effective treatment for a variety of vascular conditions.

For example, some methods can be provided in which a clinician penetrates percutaneously to a target vessel using a delivery system. The delivery system can comprise a catheter configured to access the target vessel. In some embodiments, the catheter can be a short needle. The percutaneous access can be made at a point closest to the target vessel, such as a perforator-hemorrhage site. Further, in some embodiments, an ultrasound device (such as a handheld ultrasound device) can be used as a visualization tool to facilitate placement of the needle within the target vessel.

Further, some methods can be provided in which a clinician percutaneously accesses a target vessel using a catheter. The catheter can be guided to the proper location in the target vessel using image-guided endovascular placement. The catheter can be used to deliver a device that closes or occludes the target vessel.

According to some embodiments, devices, catheters, systems, and methods disclosed herein can be used for percutaneous, peripheral occlusion of the arterial and venous vasculature. For example, some embodiments can be used to treat pelvic venous incompetence, varicocele, gonadal vein for pelvic varices in females with chronic pelvic pain, stop blood loss from a damaged blood vessel due to a traumatic arterial injury, stop hemorrhage caused by a neoplasia, and close an abnormal blood vessel or blood vessels supplying a vascular anomaly such as arteriovenous malformations or arteriovenous fistulas, and other conditions.

According to some embodiments, devices, catheters, systems, and methods disclosed herein can also be used for percutaneous, peripheral stenting of the arterial and venous vasculature.

Some embodiments disclosed herein can be used to treat various insufficiencies in the vasculature. For example, some embodiments can be used to treat venous insufficiencies in a variety of vessels of the venous anatomy, such as between deep veins and perforator veins, including the common femoral, the deep femoral, the external iliac, the femoral, the popliteal, the anterior and/or posterior tibial, and the peroneal veins.

The venous system comprises superficial veins, deep veins, and perforator veins that fluidly interconnect the superficial veins with the deep veins. Deep veins are located within the muscle fascia and allow a high volume and pressure of blood to pass therethrough, accounting for approximately 90-95% of venous blood return to the heart. Perforator veins connect the superficial and deep venous networks in the extremities, draining blood to the deep veins as part of the process of returning oxygen-depleted blood to the heart.

Perforator veins have one-way valves designed to prevent backflow of blood down towards the superficial veins. When those valves no longer function properly and reflux occurs, the buildup of blood and pressure can cause not only the superficial veins but the perforators themselves to become incompetent. Perforator veins in the lower leg and ankle are particularly vulnerable to distention and incompetence, and the resultant circulatory problems create an increased likelihood of edema, skin discoloration, dermatitis and skin ulcers in the immediate area. Perforator vessels can include: thigh perforators (perforators of the femoral canal and inguinal perforators); knee perforators (medial, lateral, supra-, and infrapatellar and popliteal fossa perforators); leg perforators (medial perforators (paratibial and lower, middle and upper posterior tibial), lateral perforators, anterior perforators, posterior perforators (gastrocnemius, intergemellar, and para-Achillean)); ankle perforators (medial, lateral, and anterior perforators); and foot perforators (medial, lateral, dorsal, and plantar perforators).

Superficial veins serve to drain blood from the skin. Blood travels from the superficial veins through the perforator veins to the deep veins. Superficial veins are located near the surface of the skin, outside of the muscle fascia, and they account for approximately 5-10% of venous blood return to the heart. There are two primary superficial veins: the small saphenous vein (SSV) and the great saphenous vein (GSV).

In accordance with some embodiments, a medical implant can be provided that can be used in a variety of clinical applications, such as vessel occlusion, stenting, or other functions within a body vessel. The medical implant can comprise a frame and one or more secondary components.

The frame can comprise one, two, or more resilient members, such as wires, rings, coils, and other components, which can be drawn out into a delivery configuration in which the frame is in a collapsed configuration and thereafter expands to an expanded state when released from a delivery device, such as a catheter.

Referring now to the figures, FIG. 1 illustrates an embodiment of an implant device 100 that can be delivered to a target location for occluding a blood vessel or body lumen. FIG. 1 illustrates a schematic cross-sectional view of a leg 90 that has a varicose vein 92. The varicose vein 92 can be a superficial vein that is interconnected to a deep vein 94 by a perforator vein 96. As illustrated, some embodiments can be used to treat varicose veins by be implanted into a perforator vein 102 that has a faulty valve. After the implant 100 is implanted into the perforator vein 102, the perforator vein 102 can be occluded, thus preventing any backflow through the perforator vein 102 and reducing or eliminating the varicose vein.

FIGS. 1B-1F illustrate schematic views of the vasculature within the legs of a human. As discussed herein, some embodiments of the system and devices can be used to treat varicose veins, such as by treating or closing incompetent venous perforators, or other circulatory afflictions, such as arteriovenous fistulae (AVF), and others. The illustrations in FIGS. 1B-1F provide further detail to illustrate potential target vessels or target areas within the legs of a patient.

Figure 2A:
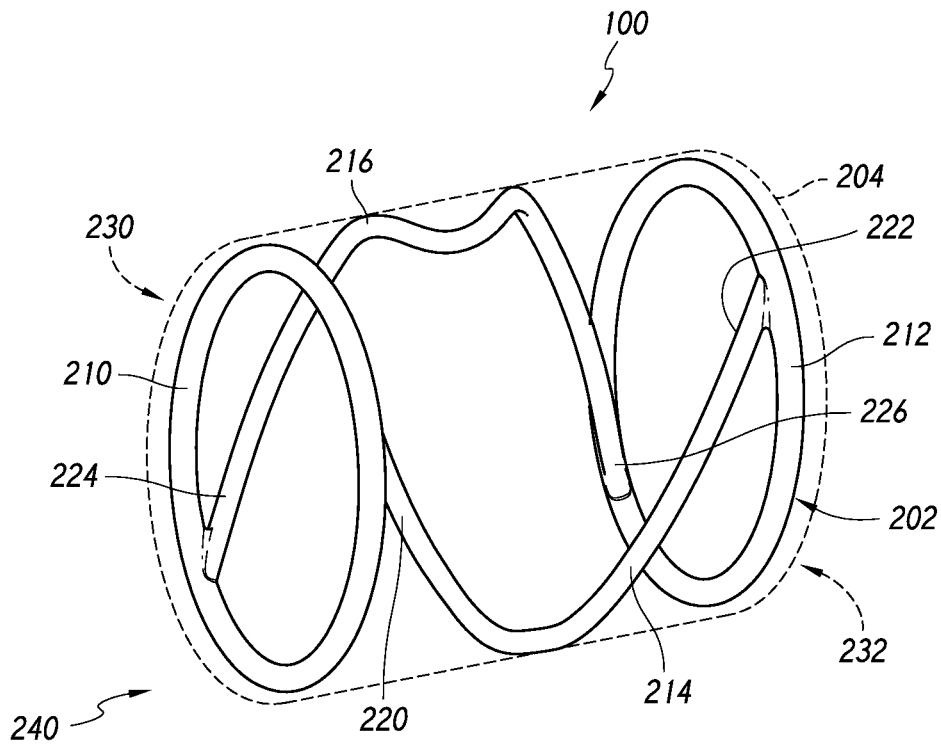
FIGS. 2A and 2B are perspective views of occlusive devices in an expanded state, according to some embodiments.
Figure 2B:
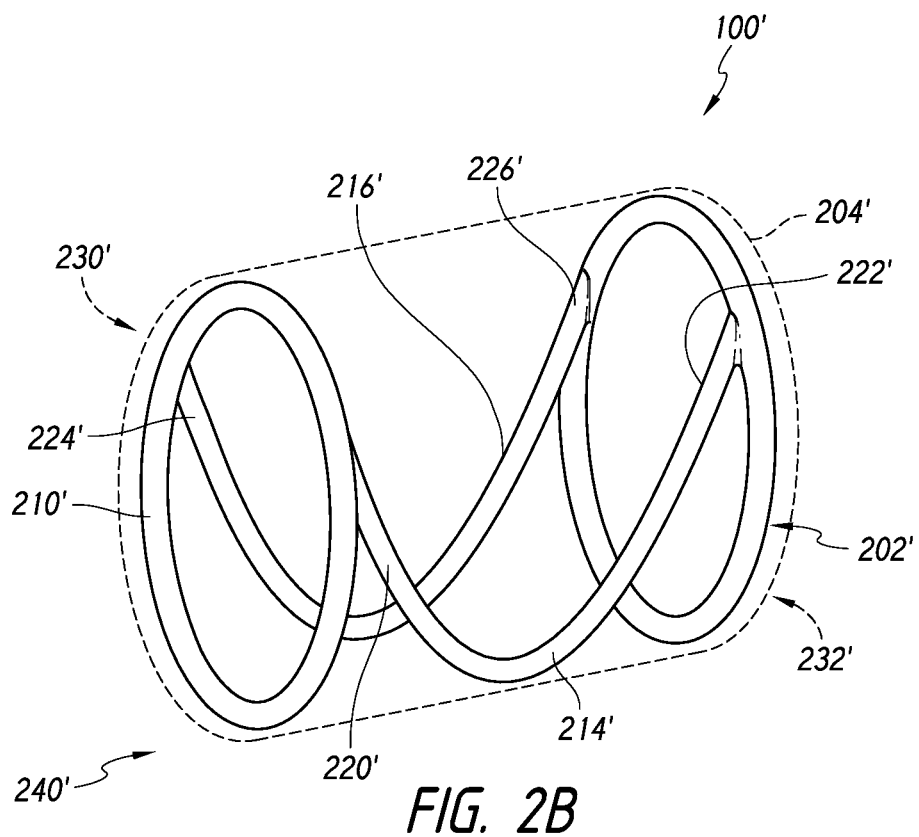

FIG. 2A-2B illustrate embodiments of the implant device 100, 100'. In referring to these embodiments, reference to FIG. 2B will be understood as referring to each element or feature as a "prime" of the mentioned feature (e.g., a device 100, 100' or frame member 202, 202'), except as otherwise indicated. The implant device can comprise a frame member 202 and an occlusive member 204. The frame member 202 can be used to anchor the occlusive member 204 within the target vessel or body lumen.

In some embodiments, the device 100 can comprise two or more support members that are coupled to at least one link member. Further, the frame member 202 can be self-expandable. In some embodiments, the frame member 202 can also be expandable under the application of force (such as by a balloon), or by electricity or heat (such as by reaching a transition temperature less than the temperature of the human body).

The frame member 202 can comprise a proximal support member 210, a distal support member 212, and at least one link member 214 extending between the proximal and distal members 210, 212. The link member 214 can be coupled to the proximal member 210 and the distal member 214 at respective first and second ends 220, 222 of the link member 214.

As shown in FIGS. 2A-2B, some embodiments can be configured to comprise a first link member 214 and a second link member 216. The second link member 216 can be coupled to the proximal and distal members 210, 212 at respective first and second ends 224, 226 of the second link member 216.

In some embodiments, the frame member can also comprise a variety of structures, including a coil that follows a helical path. Various embodiments that can be used in accordance with the inventions disclosed herein are disclosed in Applicant's co-pending patent applications: U.S. patent application Ser. No. 12/826,593, filed on Jun. 29, 2010; U.S. patent application Ser. No. 13/367,338, filed on Feb. 6, 2012; U.S. Patent Pub. No. US20120095489, published on Apr. 19, 2012; U.S. patent application Ser. No. 13/828,974, filed on Mar. 14, 2013, U.S. patent application Ser. No. 14/044,794, filed on Oct. 2, 2013; U.S. Patent App. No. 61/835,406, filed on Jun. 14, 2013; U.S. Patent App. No. 61/904,376, filed on Nov. 14, 2013; U.S. Patent App. No. 61/904,379, filed on Nov. 14, 2013; U.S. Patent App. No. 61/835,461, filed on Jun. 14, 2013; U.S. Patent App. No. 61/900,321, filed on Nov. 5, 2013; and U.S. patent application Ser. No. 14/101,171, filed on Dec. 9, 2013, the entireties of which are incorporated herein by reference.

The occlusive member 204 can be coupled to the frame member 202 can be configured to facilitate at least partial occlusion of the target vessel into which the device 100 is placed. In some embodiments, the occlusive member 204 can comprise an ePTFE membrane or cap that extends around and/or is coupled to the frame member 202.

The occlusive member 204 can comprise a proximal end portion 230 and a distal end portion 232. At least one of the proximal end portion 230 and the distal end portion 232 can be coupled to the frame member 202. For example, in some embodiments, the occlusive member 204 can be coupled to the frame member 202 and/or be configured as illustrated in applicant's co-pending U.S. patent application Ser. No. 14/101,171, filed Dec. 9, 2013 (084988-0046); Ser. No. 14/044,794, filed on Oct. 2, 2013 (084988-0039); and Ser. No. 13/828,974, filed on Mar. 14, 2013 (084988-0030), the entirety of which is incorporated herein by reference.

Figure 3A:
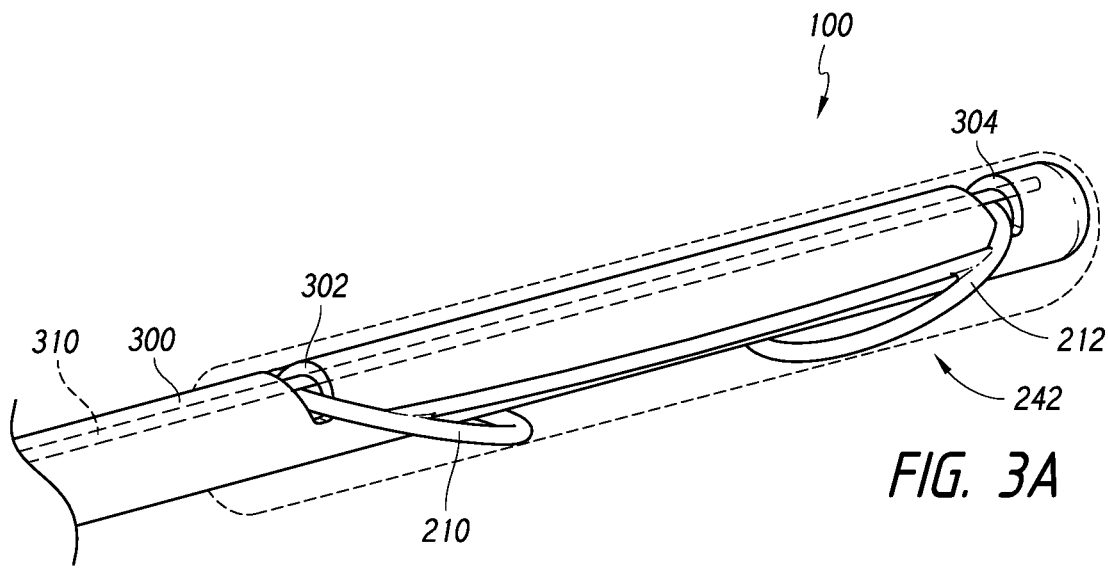
FIGS. 3A-3C illustrate sequential steps in releasing the occlusive device of FIG. 2A from engagement with a catheter, according to some embodiments.

The frame member 202 is illustrated in the expanded state 240 in FIG. 2A-2B. According to some embodiments, the frame member 202 can be resiliently deflectable from the expanded state 240 to a collapsed state 242, illustrated in FIG. 3A. Other embodiments illustrated in the figures demonstrate the change from the collapsed state to the expanded state, and similar principles of operation can be implemented in yet additional embodiments.

According to some embodiments, the collapsed state of the device can enable the device to be delivered to a target vessel in a low profile size. Subsequently, the device can expand, such as by self-expansion or otherwise, in order to be released and anchored in the target vessel.

Some embodiments can be configured such that proximal and/or distal end portions of the implant expand to a diameter much greater than a diameter of a central portion of the implant such that expansion of the implant reduces or eliminates one or more degrees of motion of the device relative to surrounding vasculature.

For example, as illustrated in FIG. 1A, proximal and distal end portions 110, 112 of the device 100 have been expanded radially relative to a central portion 114 of the device 100. Thus, when placed in the perforator vein 96, the distal end portion 112 of the device 100 can be released and expanded into the deep vein 94 and the proximal end portion 110 of the device 100 can be released and expanded into the superficial vein 92, thus causing the central portion 114 of the device 100 to reside within the perforator vein 96. This expansion of the device 100 can provide partial or full occlusion of the perforator vein 96.

In some embodiments, the device can be configured to be resiliently biased toward an expanded configuration. Thus, the device can be loaded onto a catheter or other delivery mechanism in a delivery or collapsed configuration and, when released, be expanded or spring back to the expanded configuration in the target vessel.

Further, in accordance with some embodiments, the one or more link members can be configured to exert an active foreshortening force between the proximal and distal end portions when the device is in the expanded configuration.

The one or more link members can be shaped in way that upon release from the delivery mechanism, each link member tends to bring opposing support members together as close as possible by springing back or rebounding into a predetermined V or parabola shape. Thus, in the collapsed configuration, each link member can be elongated or stretched along the longitudinal axis in a state of tension. When the device is released from constraint and allowed to expand towards the expanded configuration, each link member can return to a predetermined shape, causing the length of the device to become foreshortened.

For example, in the embodiment illustrated in FIG. 1, the central portion 114 of the implant 100 can comprise one or more link members that tend to draw the proximal and distal end portions 110, 112 toward each other, thus foreshortening the length of the implant 100. In this manner, the device 100 can be placed at a target vessel (shown as a perforator vessel 96) and longitudinally contract in order to more securely engage the target vessel, provide better occlusion of the target vessel, and reduce obstruction of adjacent vessels (such as the superficial and deep vessels 92, 96).

Some embodiments can foreshorten by between about 10% and about 90% of the length of the device 100 in the collapsed state 242. The collapsed length of the device 100 can be measured either using the furthest points of opposing ends or using the points at which the link member(s) interconnects with the proximal and/or distal members.

The length of each link member as set and deployed, which can determine the distance between adjacent rings in the expanded configuration (manifesting the vessel closure position) can be between about 3 mm and about 20 mm, between about 4 mm and about 15 mm, between about 6 mm and about 12 mm, between about 8 mm and about 10 mm, or between about 4 mm and about 10 mm. Accordingly, in the collapsed configuration, the length of each link member can be correspondingly increased based on the geometry of the link member in the expanded configuration versus in the collapsed configuration.

In some embodiments, in the expanded configuration, a length of the frame member 202 may be between about 7 mm and about 15 mm, between about 8 mm and about 12 mm, or between about 9 mm and about 10 mm.

As illustrated in embodiments disclosed herein, the device can comprise two or more link members. The link members can, when seen in side view, have a generally V or parabolic shape. The link members can extend helically about the periphery, outer surface, or circumference of the device. In some embodiments, a path of a link member can reverse direction, such as a helical path reversing pitch, as the link member extends between support members.

Figure 5:
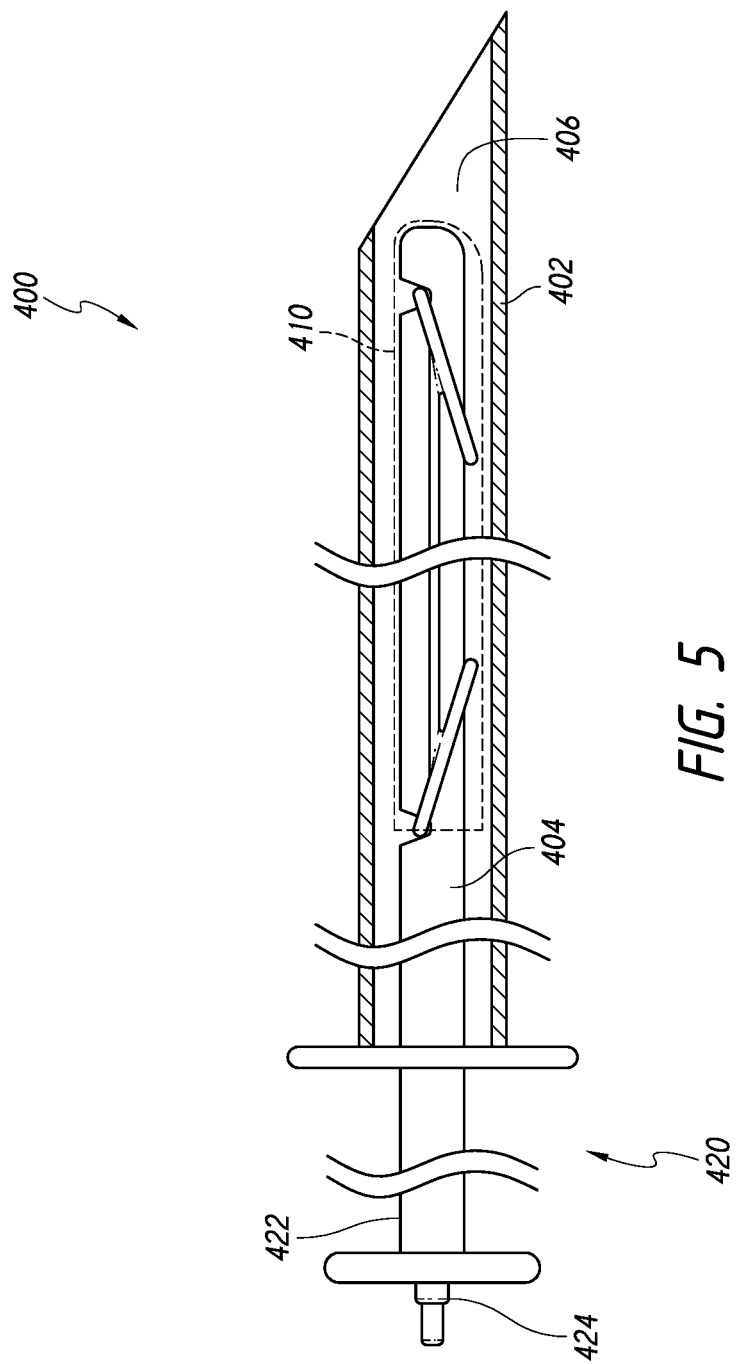
FIG. 5 is a side, cross-sectional view of a deployment system comprising a needle, a catheter, and an occlusive device, according to some embodiments.

For example, as illustrated in FIG. 2A-2B, the link members 214, 216 can be configured to extend about the periphery or circumference of the frame member 202. FIG. 2A illustrates that the link members 214, 216 can extend about the periphery or circumference of the frame member 202 in substantially parallel helical directions. FIG. 2A also illustrates that the pitch of the helical direction can be reversed, for example, at about a midpoint of the link member. Further, as illustrated in FIGS. 2B and 5, the link members can be configured to extend about the periphery or circumference of the frame member in substantially opposite helical directions.

In accordance with some embodiments, in order to achieve the expanded state 240, the frame member 202 can be configured such that interactions between its component parts and material properties of the component parts tend to create a preferred or default position to which the frame member 202 resiliently expands. Further, in some embodiments, the frame member 202 can be deflectable and deformable from the collapsed configuration to the expanded configuration in order to deliver the device to the target vessel.

Figure 3B:
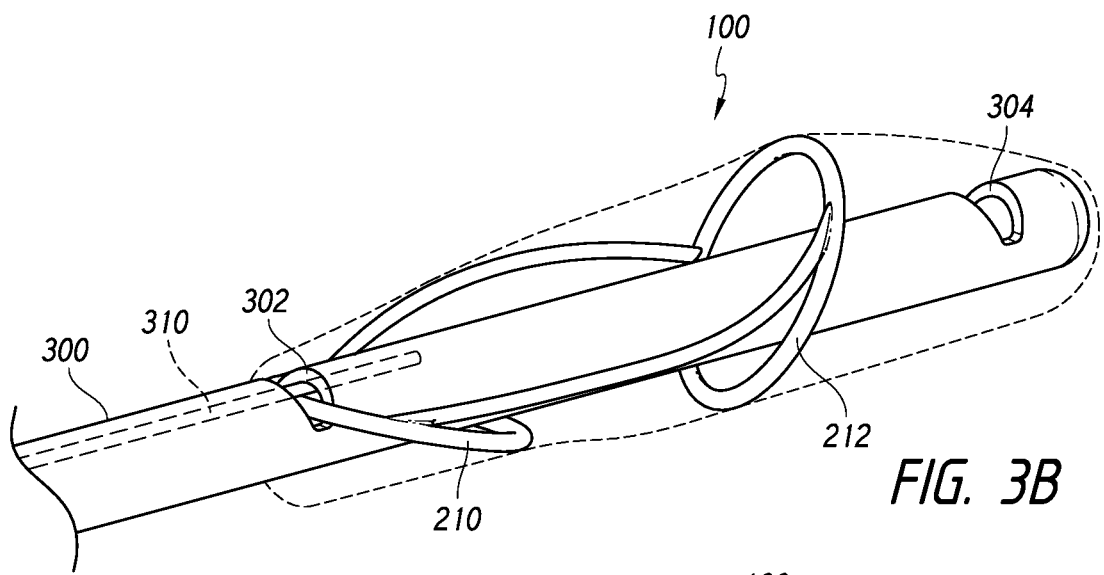
Figure 3C:
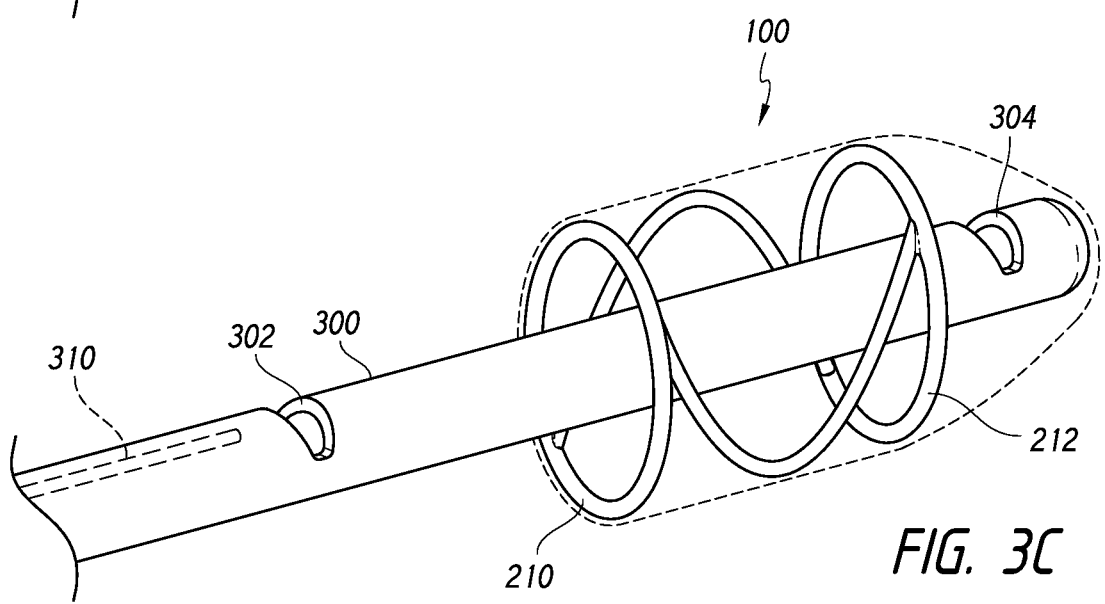

In some embodiments, a first plane passing through the proximal member 210 and a second plane passing through the distal member 212 can each undergo a rotational or angular movement relative to the longitudinal axis when the frame member 202 moves from the collapsed configuration 242 to the expanded configuration 240. This movement is shown generally in FIGS. 3A-3C.

Figure 4A:
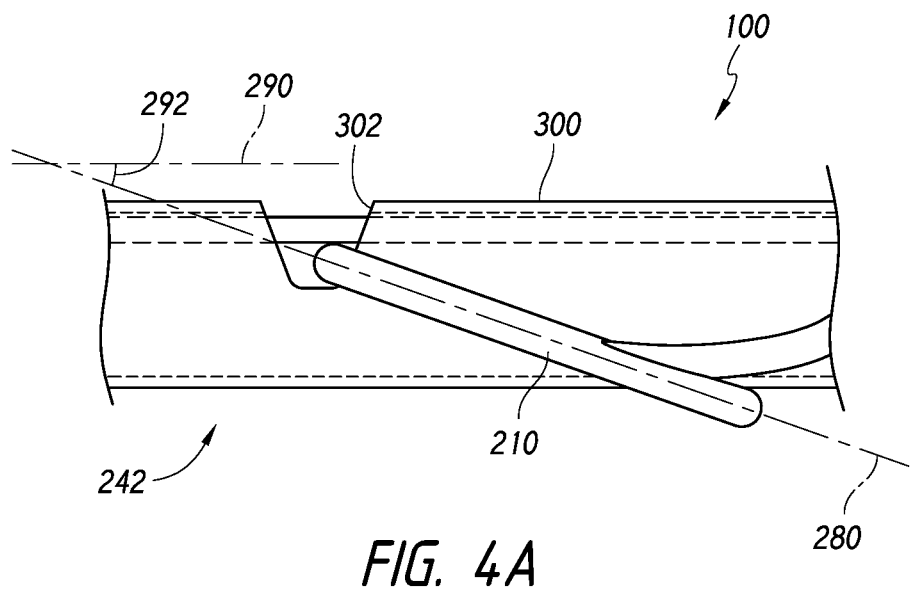
FIGS. 4A-4B illustrate side views of the engagement between the proximal and distal end portions of the occlusive device as shown in FIG. 3A.
Figure 4B:
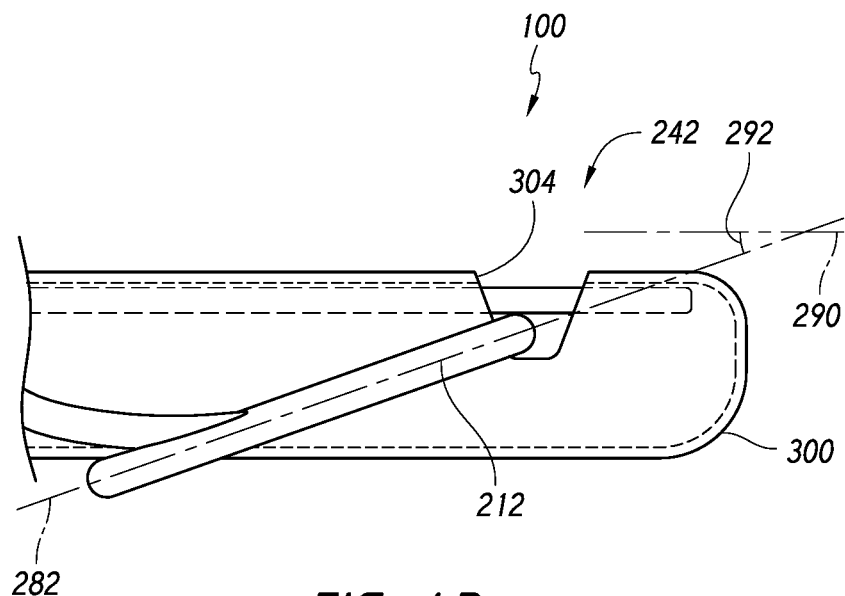

For example, in the collapsed configuration 242, the frame member 202 can be configured such that at least one of the proximal member 210 or the distal member 212 extends substantially parallel or oblique relative to a longitudinal axis of the device 100. When the proximal member 210 and/or the distal member 212 move(s) from the collapsed configuration 242 to the expanded configuration 240, the first and/or second plane(s) can move angularly or rotate relative to the longitudinal axis. For example, as illustrated in FIGS. 4A-4B, a first plane 280 can pass through the proximal member 210, and a second plane 282 can pass through the distal member 212. When the implant 100 is released from the collapsed configuration 242 to the expanded configuration 240, the first and second planes 280, 282 can move or rotate relative to the longitudinal axis 290. For example, in some embodiments, the first and second planes 280, 282 can be substantially perpendicular relative to the longitudinal axis 290.

The first and/or second planes can be arbitrary planes that correspond to the respective proximal and distal members. The location or orientation of the planes relative to the members can each be determined based on shape, size, or other characteristics of the members. For example, the planes can each pass through a maximal amount or mass of the respective members. Further, the planes can also be defined by one or more surface features of the members. For example, if the members comprise planar annuli, a top or bottom surface of each annulus can serve to define the extent of the plane.

The degree of rotation or angular movement of the first and/or second planes can be between about 10° and about 170°, including any of the angular ranges or angles therebetween, which will not be listed here for brevity.

For example, plane(s) passing through the proximal or distal member can be oriented within about 45° or less of the longitudinal axis when in the collapsed configuration 242. For example, as illustrated in FIGS. 4A-4B, a first plane 280, passing through the proximal member 210, and a second plane 282, passing through the distal member 212, can each be oriented within about 45° or less of the longitudinal axis 290. The angle of the planes is shown as element 292 in FIGS. 4A-4B.

The degree of rotation or angular movement, as well as the degree of foreshortening, can be measured based on the movement of the proximal and/or distal members outside of the body or when placed in situ.

In accordance with some embodiments, the support members (e.g., the proximal and distal members 210, 212) can be configured to pop up post-deployment in order to provide reliable closure of the target vessel or hole. Further, because a target vessel may be fairly short (such as in the case of a venous perforator vessel), the device can be configured to draw opposing ends thereof into a foreshortened configuration. The support members can comprise rings that can be made as solid shapes or as open spirals.

Each support member can have a maximum cross-sectional dimension of between about 6 mm and about 20 mm. In some embodiments, the maximum cross-sectional dimension can be between about 8 mm and about 16 mm, between about 10 mm and about 15 mm, between about 12 mm and about 14 mm, between about 8 mm and about 12 mm, or between about 10 mm in 15 mm. In some embodiments, each support member can be configured as a circular or annular shape. Accordingly, a support member can define a diameter in any of the above-noted ranges. Further, the support member can be deflectable and the maximum cross-sectional dimension can represent the maximum cross-sectional dimension of the support member in the expanded configuration. Therefore, the support member can be deflected such that a deflected cross-sectional dimension in the collapsed configuration is greater than the maximum cross-sectional dimension in the expanded configuration.

In the expanded configuration, a cross-sectional dimension of the proximal and distal end portions of the device (due to the cross-sectional dimension of the corresponding support member) can be greater than a cross-sectional dimension of a central portion of the device. For example, a cross-sectional dimension of the central portion 114 can be between about 2 mm and about 10 mm. Thus, when in the expanded configuration, the central portion 114 can have a cross-sectional dimension that is less than the cross-sectional dimensions of the proximal and/or distal end portions of the device. Such an embodiment as illustrated in FIGS. 1 and 8A-8D. The embodiments illustrated in FIGS. 2A-2B, 3C, 5, 6C, and 9C are shown in expanded configurations that are not deployed into or constrained by a corresponding target vessel geometry. When implanted into a corresponding target vessel, the geometry of the target vessel can tend to constrict the cross-sectional dimension of the device in the central portion thereof, as shown in FIGS. 1 and 8A-8D.

Delivery of the implant device can be performed using a delivery system that maintains the implant device in a constrained or collapsed configuration while being advanced to the target area. The delivery system can carry the implant device in the collapsed configuration until reaching the target area and thereafter be actuated to release the implant device at the target area. The actuation of the delivery system can be performed in accordance with some of the embodiments disclosed herein. Further, in accordance with some embodiments, the delivery system can comprise a catheter or a needle delivery member.

As illustrated in FIGS. 3A-4B, the frame member 202 of the device 100 (referring to the embodiment in FIG. 2A, although any of the embodiments disclosed herein can be used with any of the delivery systems disclosed herein) can be configured to be supported or engaged by a distal end of a catheter 300. The catheter 300 can comprise at least one notch that facilitates engagement between the frame member 202. The frame member 202 comprises proximal and distal members 210, 212 that can be engaged within the respective proximal and distal notches 302, 304. For example, the delivery system can comprise an actuation wire 310 that can extend through a lumen of the catheter 300 in order to engage the respective proximal and distal members 210, 212.

The actuation and function of the delivery system can incorporate features disclosed in Applicant's co-pending patent application Ser. No. 14/101,171, filed Dec. 9, 2013 (084988-0046); Ser. No. 14/044,794, filed on Oct. 2, 2013 (084988-0039); and Ser. No. 13/828,974, filed on Mar. 14, 2013 (084988-0030), the entireties of each of which are incorporated herein by reference.

According to some embodiments, the device can be engaged, supported, and/or housed along a distal portion of the system. Some embodiments can advantageously provide a needle delivery member that has a small cross-sectional profile.

For example, the needle or needle delivery member can comprise a needle profile that defines an outer diameter from about 3 Fr, 4 Fr, 5 Fr, 6 Fr, 7 Fr, 8 Fr, or 9 Fr, as noted in Table 1 below and discussed further herein.

TABLE 1

| French Gauge | Diameter (mm) | Diameter (inches) |
| --- | --- | --- |
| 3 | 1 | 0.039 |
| 4 | 1.33 | 0.053 |
| 5 | 1.67 | 0.066 |
| 6 | 2 | 0.079 |
| 7 | 2.3 | 0.092 |
| 8 | 2.7 | 0.105 |
| 9 | 3 | 0.118 |

FIG. 5 illustrates an embodiment of a delivery system 400 for delivering an implant device to a target vessel. The delivery system 400 can comprise a needle component 402 and a catheter 404 that is slidably mounted within a lumen 406 of the needle component 402. The catheter 404 can support an implant device 410 in the manner described above with respect to FIGS. 3A-3B.

As illustrated in FIG. 5, the system 400 can comprise a handle portion 420 that is coupled to the needle component 402. The handle portion 420 can comprise an actuating mechanism 422 that can be operative to control proximal or distal movement of the catheter 404. Additionally, the handle portion can comprise an implant release component 424 that can be coupled to a proximal end of the actuation wire 310 (shown in FIGS. 3A-3C).

In use, the delivery system 400 can be advanced to a target vessel, such as an incompetent perforator vessel that is to be closed. The needle component 402 can be advanced into the tissue of the patient and delivered as illustrated in FIGS. 6A-6D.

Figure 6A:
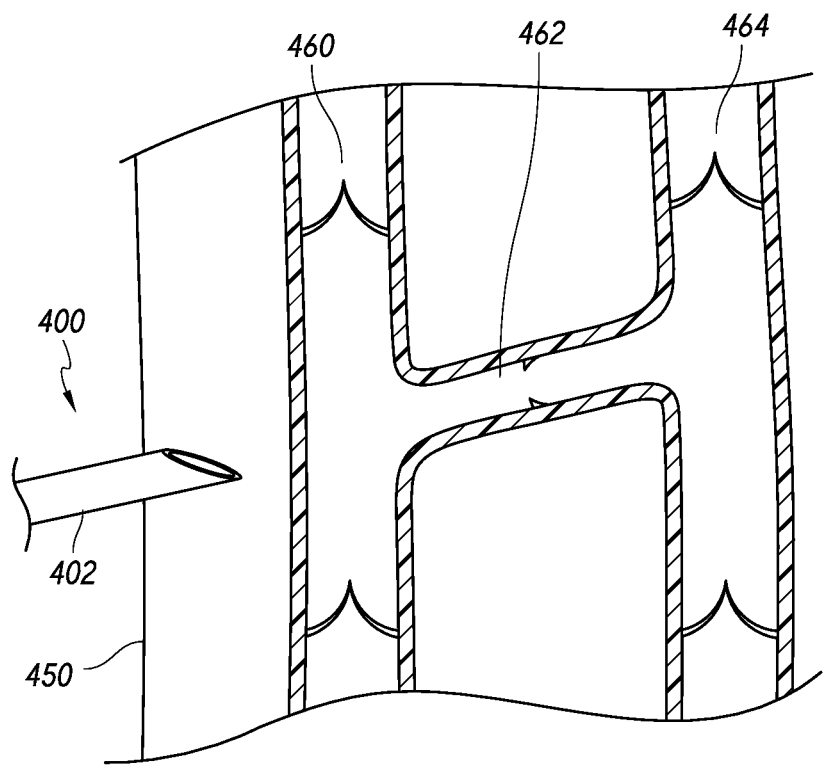
FIGS. 6A-6D illustrate sequential steps in implanting an occlusive device in a perforator vessel, according to some embodiments.
Figure 6B:
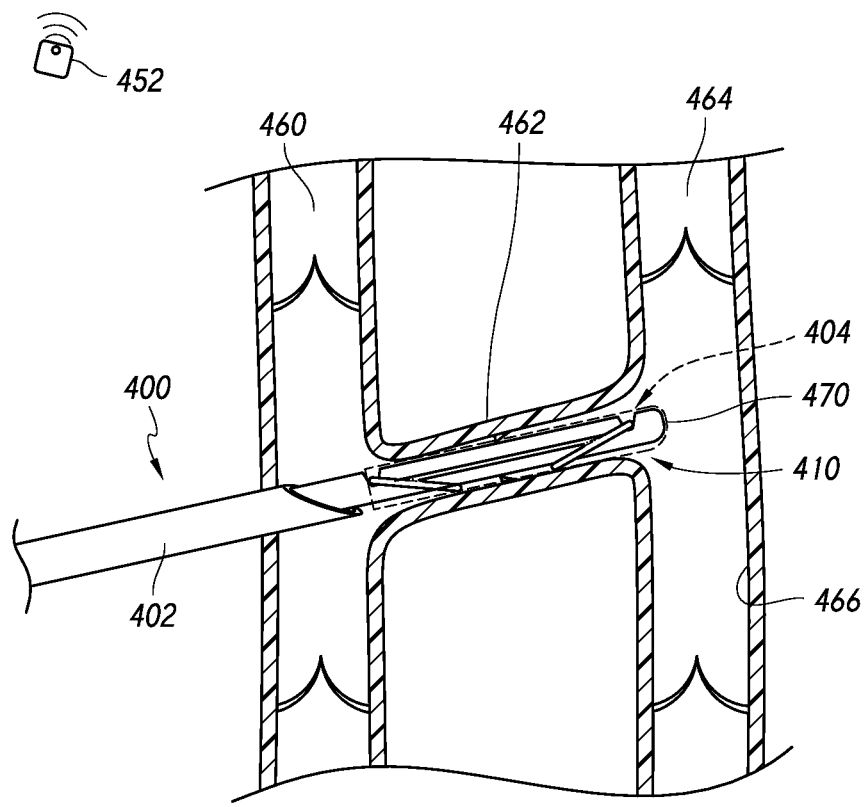

As shown in FIGS. 6A-6B, the delivery system 400 can be introduced through the skin 450 with image guidance provided by a hand held ultrasound system 452. For example, in some embodiments, a scope, vessel finder, or vessel transiluminator, such as a Venoscope®, can be used to locate the target veins or arteries. A guidewire can be introduced into a superficial vein 460, which can be used to facilitate introduction of a needle component 402. The needle component 402 can be advanced into the superficial vein 460 toward a perforator vein 462 that interconnects the superficial vein 460 with a deep vein 464. FIG. 6B illustrates that once the needle component has been guided into the perforator vein 462, the catheter 404, with the implant 410 supported thereon, can be advanced until a distal end 470 of the catheter 404 enters or is positioned adjacent to the deep vein 464. The distal end 470 can be advanced until it is positioned within the deep vein 464, adjacent to an inner wall 466 of the deep vein 464, or at least is placed deep inside of the perforator vein 462, which can be aided by ultrasound visualization.

Figure 6C:
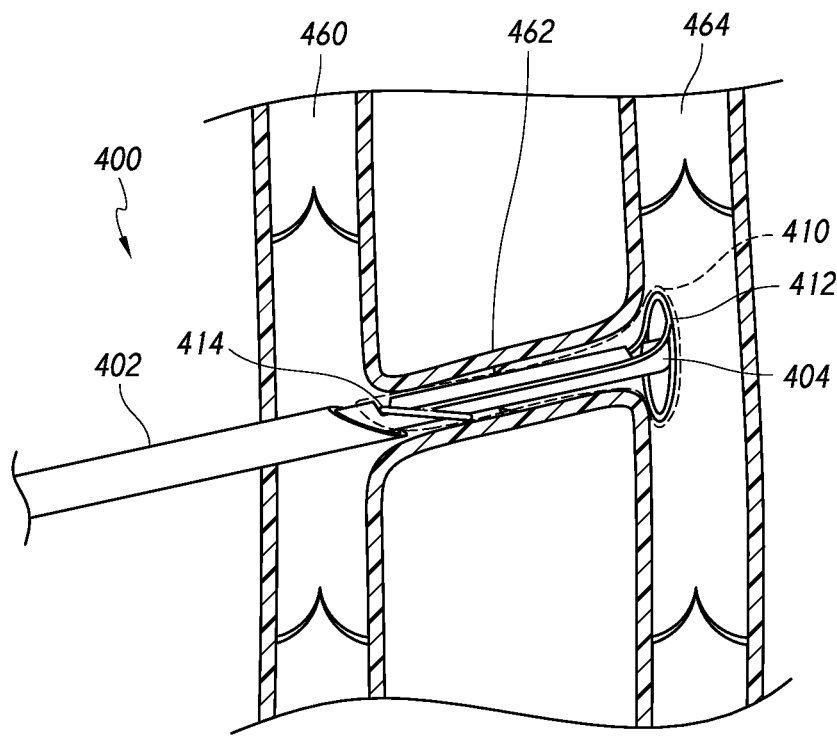
Figure 6D:
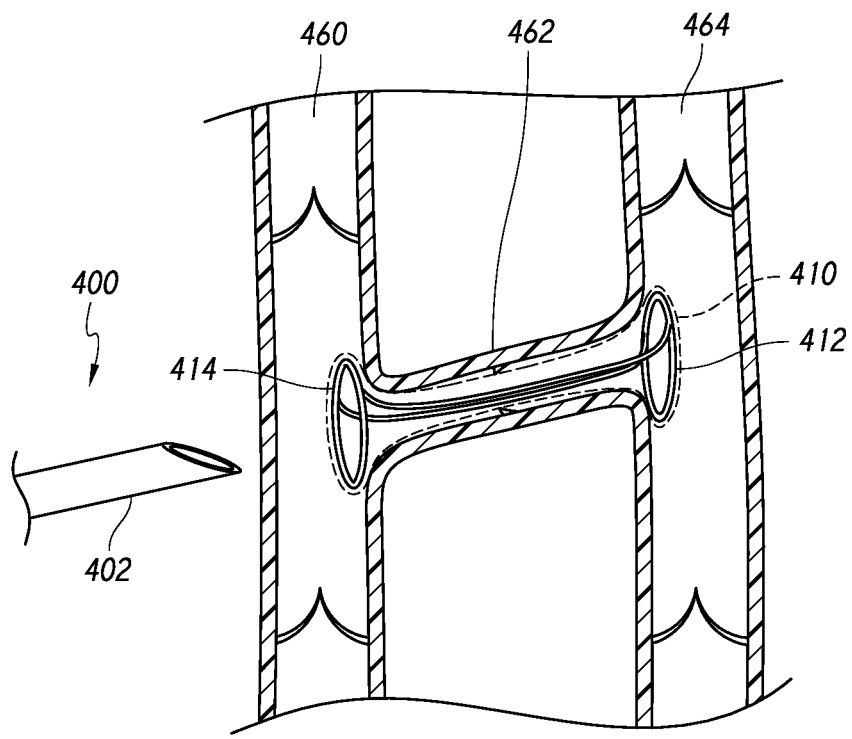

Once the distal end 470 of the catheter 404 is in the proper position within the deep vein 464, the implant distal portion 412 can be released from engagement with the catheter 404. In order to release the implant device 410, the distal end portion 412 can be released as shown in FIG. 6C. Thereafter, a proximal end portion 414 of the implant device 410 can be released and permitted to expand into the superficial vein 460. The needle component 402 thereafter can be proximally withdrawn out of the perforator vein 462, as illustrated in FIGS. 6C-6D. As the implant device 410 moves towards its expanded configuration, the proximal and distal end portions 412, 414 can be drawn together by virtue of the foreshortening created by the link member(s) of the implant device 410. Thus, closure of the perforator vein 462 can occur immediately or instantaneously after release of the proximal end portion 414 of the device 410.

In case of occlusion of AVF, the delivery system can be configured similarly to that described above with respect to FIGS. 5-6D. The delivery system can optionally deliver the implant device using a catheter and image guided endovascular intervention. For example, the delivery system in the case of AVF can achieve access through traditional pathways, such as the femoral or jugular artery, or other appropriate pathways, and be advanced toward the target area. In such embodiments, the profile of the catheter can be about 3 Fr, 4 Fr, 5 Fr, 6 Fr, or 7 Fr.

Figure 7:
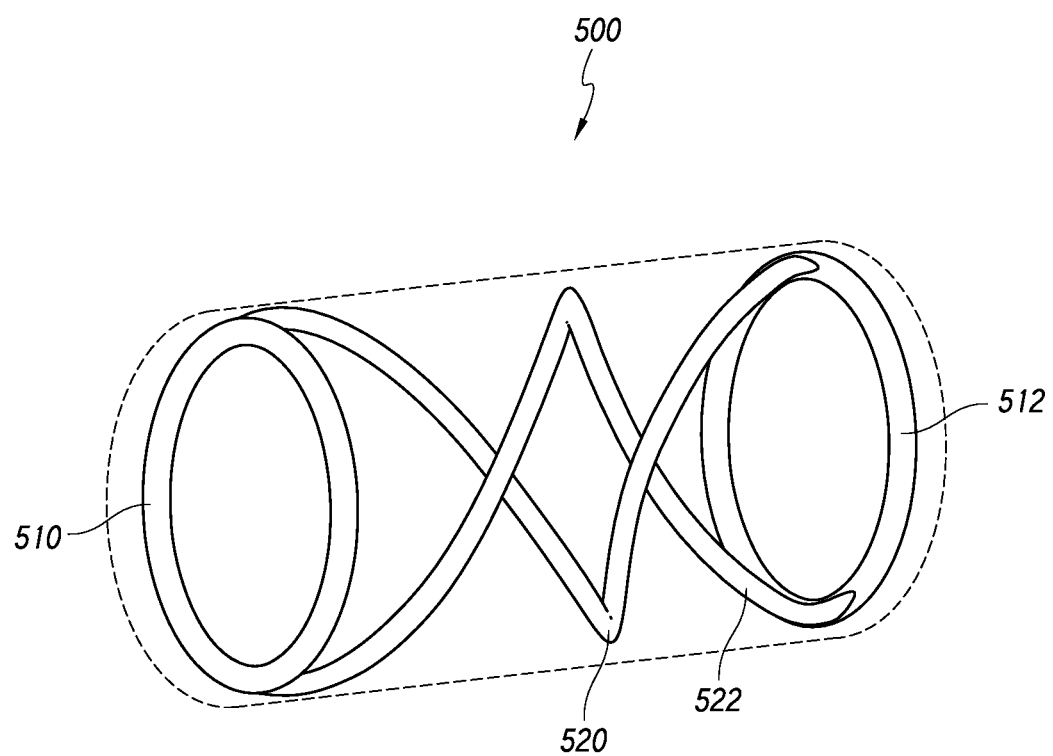
FIG. 7 is a perspective view of another occlusive device in an expanded state, according to some embodiments.
Figure 8A:
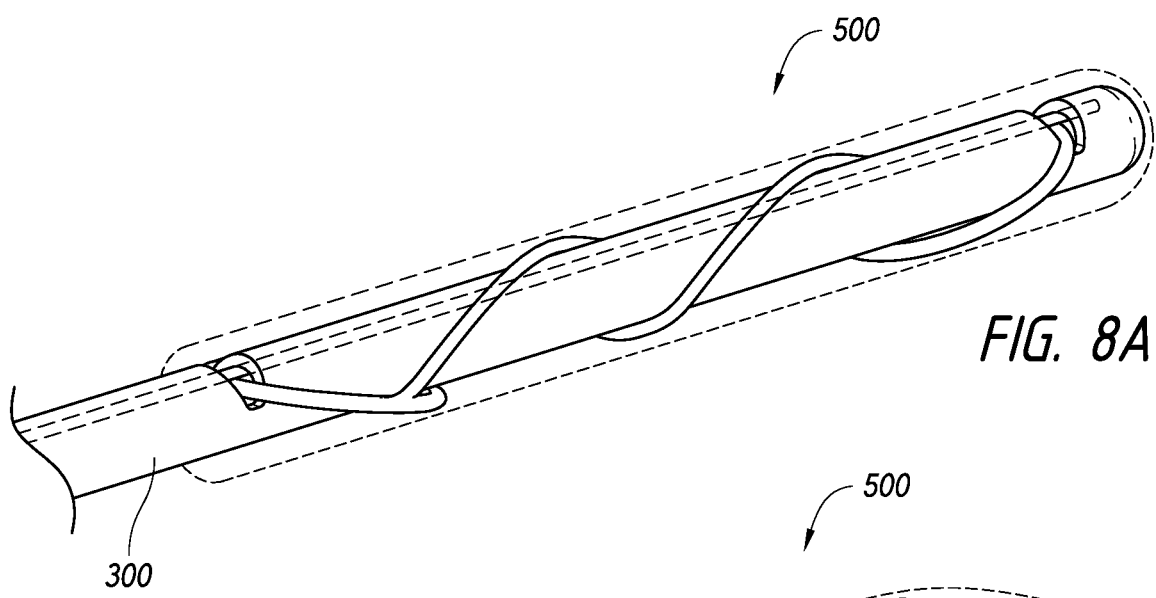
FIGS. 8A-8C illustrate sequential steps in releasing the occlusive device of FIG. 5 from engagement with a catheter, according to some embodiments.
Figure 8B:
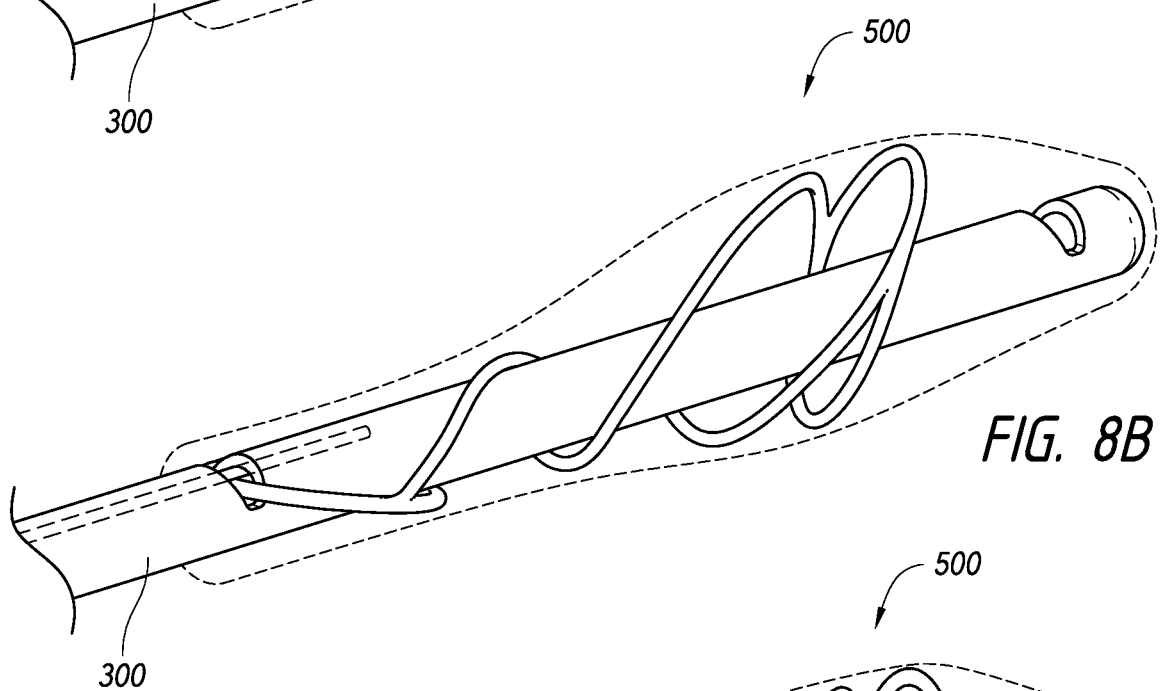
Figure 8C:
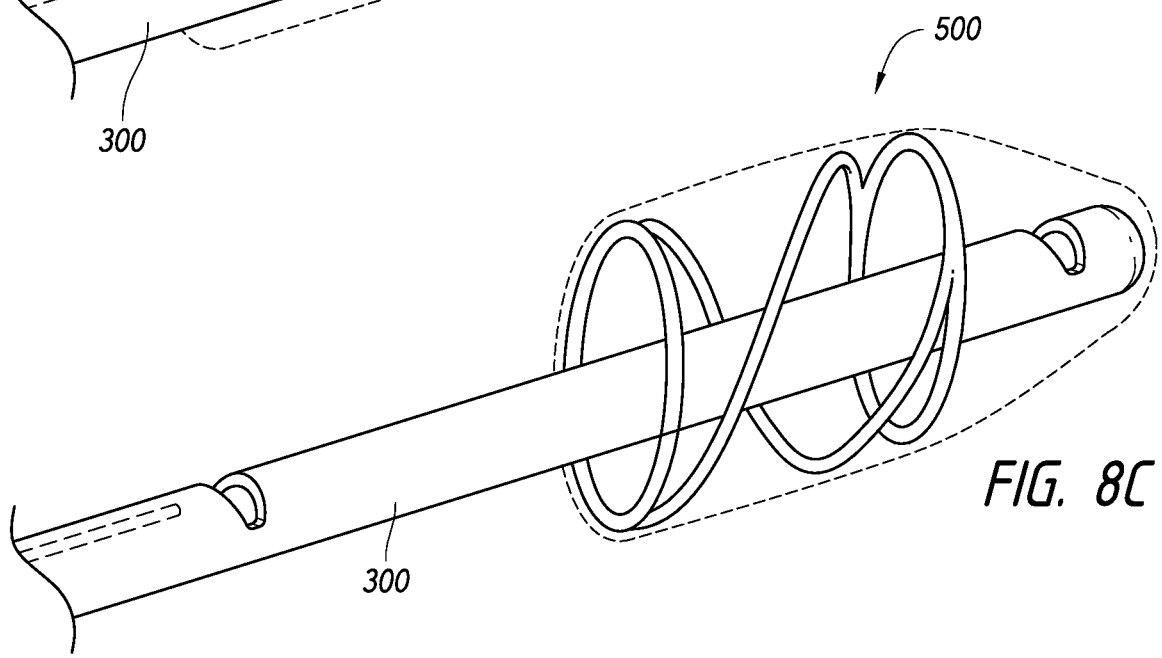

Referring now to FIGS. 7-8C, another occlusive device 500 is shown in expanded and collapsed configurations, and in relationship to a catheter 300 on which the device 500 can be supported. The device 500 comprises proximal and distal members 510, 512 and a pair of link members 520, 522. The link members 520, 522 can be coupled to the proximal and distal members 510, 512 and extend in a helical direction about the periphery or circumference of the device 500. As shown, the link members 520, 522 can extend in opposing helical directions. However, as illustrated in the embodiment shown in FIG. 2A, some embodiments can be configured such that the link members extend in the same helical direction. Additional details and features related to the operation and interaction of the device 500 with the catheter during expansion or release of the device 500 similar to those described above with respect to FIGS. 3A-3C and will not be repeated here and for brevity.

Figure 9A:
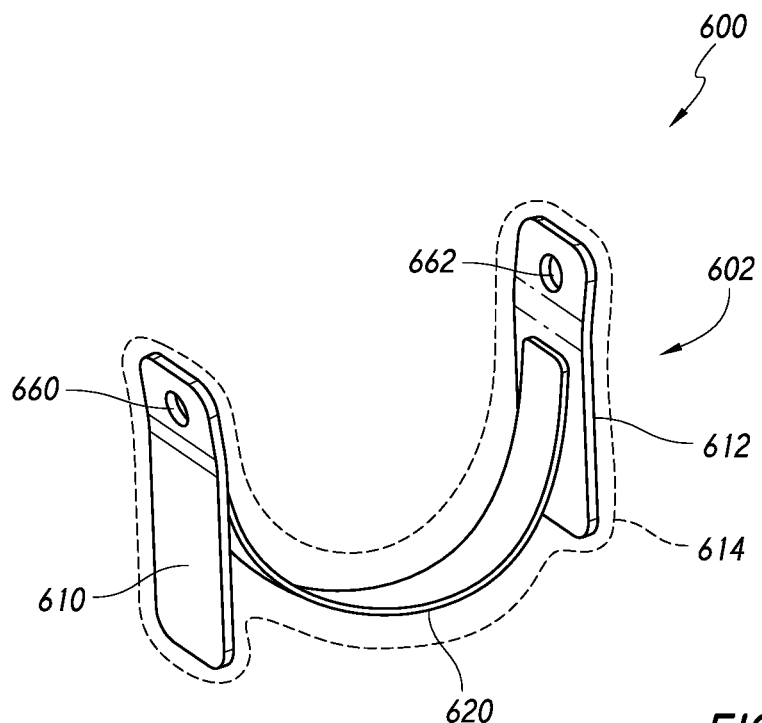
FIG. 9A illustrates a perspective view of an occlusive device in an expanded position, according to some embodiments.
Figure 9B:
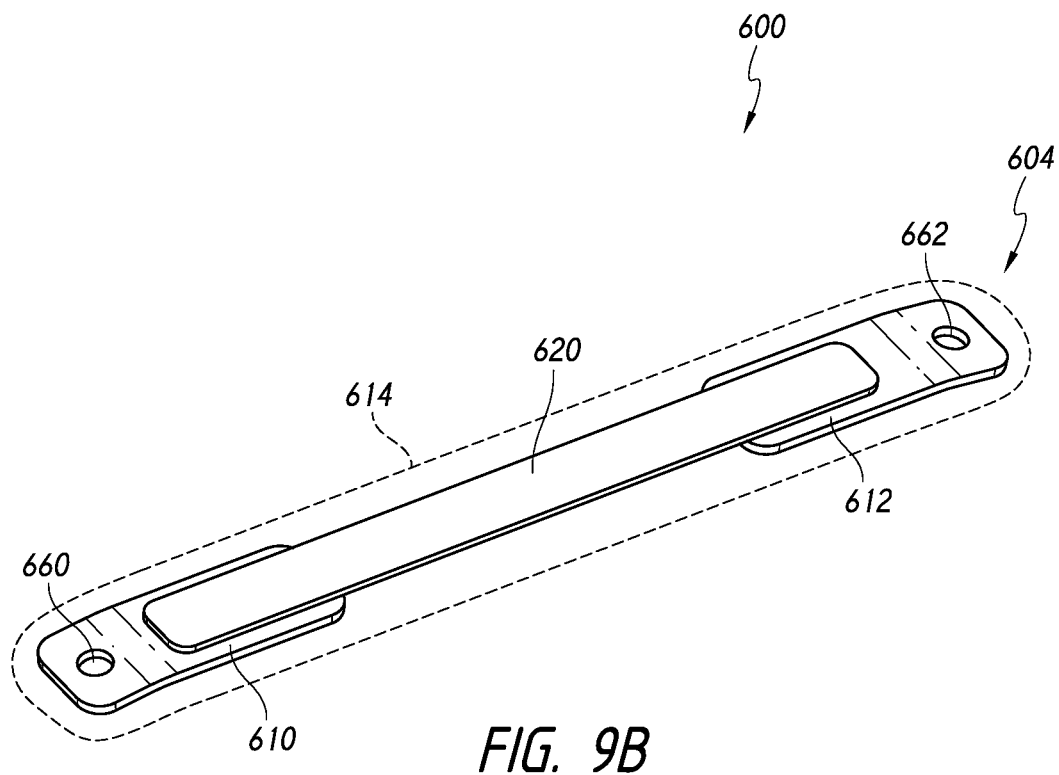
FIG. 9B illustrates a perspective view of an occlusive device in a collapsed position, according to some embodiments.

FIGS. 9A-9B illustrate perspective views of another embodiment of an occlusive device 600, in an expanded configuration 602 and in a collapsed configuration 604. The device 600 can comprise a proximal member 610 and a distal member 612, as well as an occlusive member 614. The proximal and distal members can be interconnected by at least one link member 620. The device 600 can incorporate many of the features and advantages discussed above with respect to the devices shown in FIGS. 1-8C, in such features will not be discussed here and for brevity.

Figure 10A:
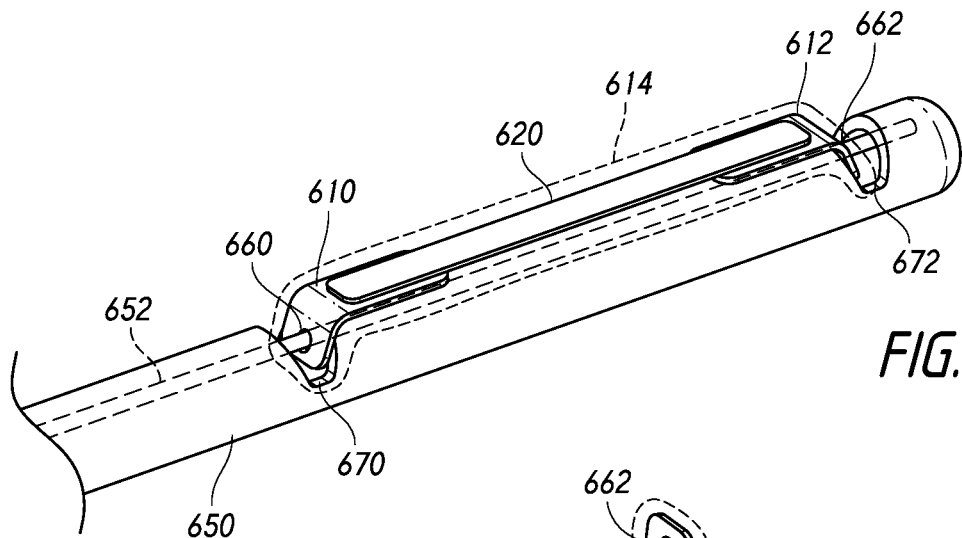
FIGS. 10A-10C illustrate sequential steps in releasing an occlusive device from engagement with a catheter, according to some embodiments.
Figure 10B:
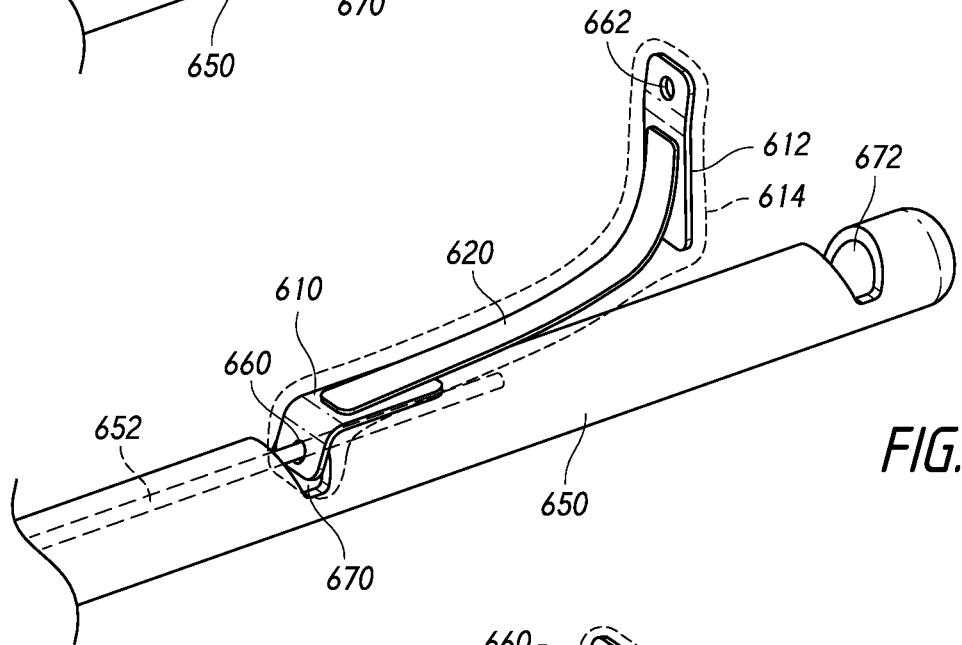
Figure 10C:
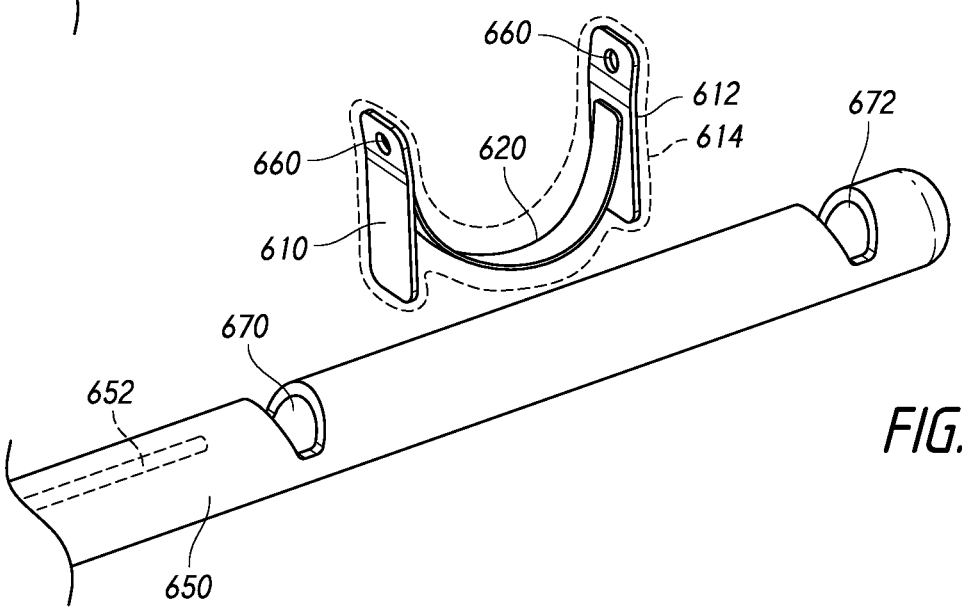

The link member 620 can be configured to rebound or assume a U- or V-shaped configuration when in the expanded configuration 602. The device can be coupled to a catheter 650 and released there from when delivered to the target vessel, as illustrated in FIGS. 10A-10C.

In accordance with some embodiments, in order to facilitate engagement with the catheter 650, the device 600 can comprise proximal and distal apertures 660, 662 configured to be engaged with an actuation wire 652 at respective first and second slots 670, 672 of the catheter 650. The implant device 600 can be coupled to the catheter as illustrated in FIG. 10A. In order to release the device 600, the actuation wire 652 can be proximally withdrawn within the catheter 650 until the distal and proximal members 612, 610 are sequentially released from engagement with the catheter 650. This embodiment can provide the advantageous functions illustrated in discussed above with respect to the other devices and delivery systems.

Figure 11A:
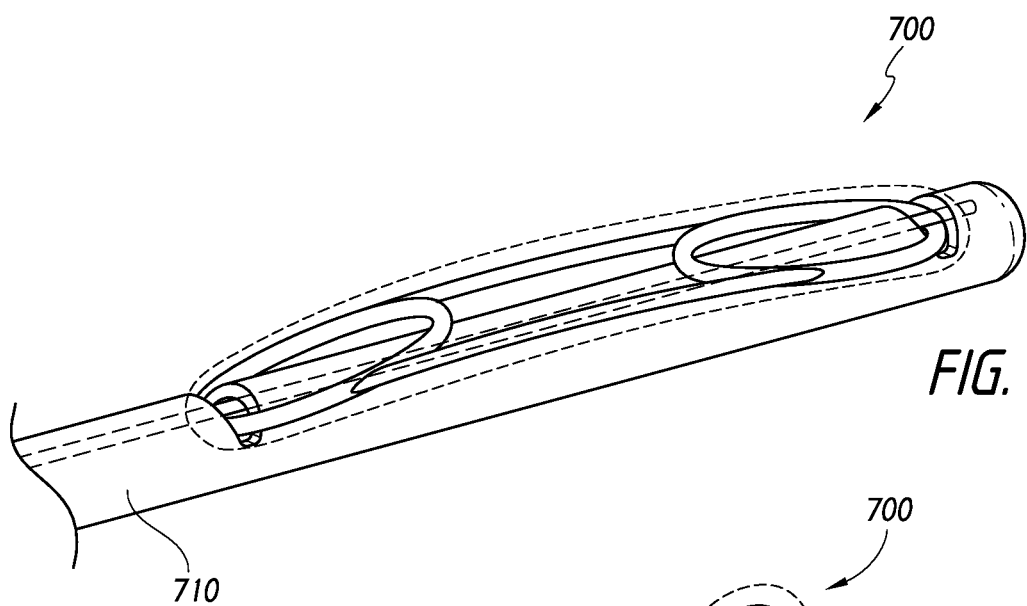
FIGS. 11A-11C illustrate sequential steps in releasing an occlusive device from engagement with a catheter, according to some embodiments.
Figure 11B:
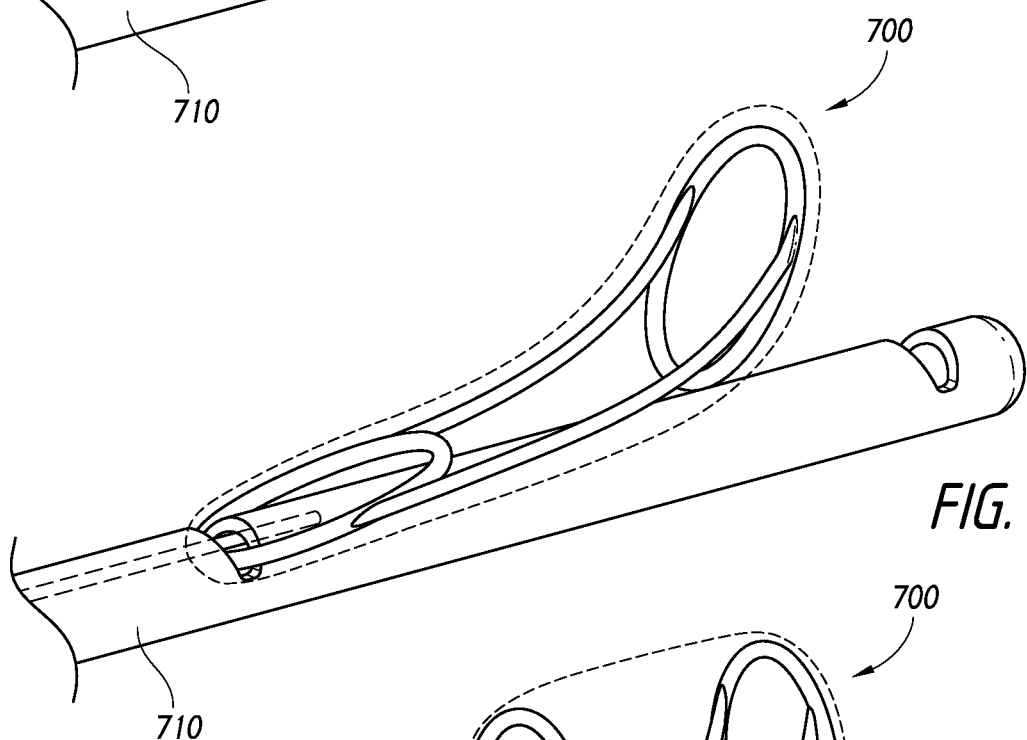
Figure 11C:
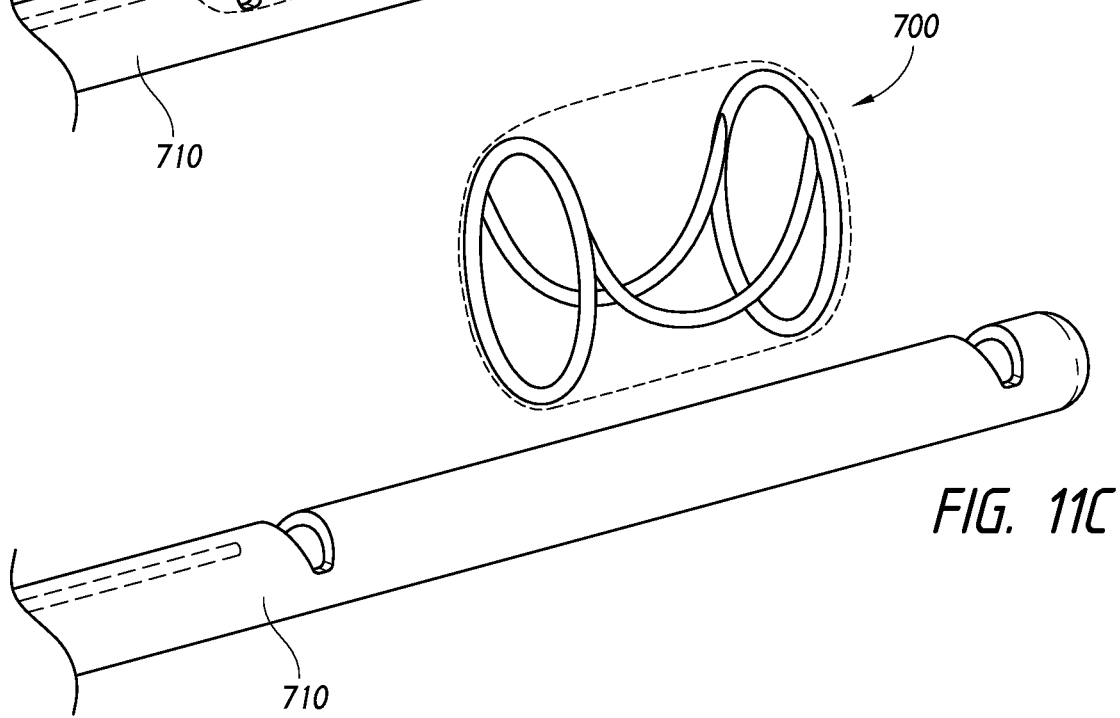

In accordance with yet another embodiment, FIGS. 11A-11C illustrate sequential steps in releasing an occlusive device 700 from engagement with a catheter 710. The device 700 is configured as discussed above with respect to the device 100' shown in FIG. 2B. Accordingly, the discussion herein for the device 100' is incorporated here and will not be repeated for brevity. FIGS. 11A-11C illustrate another delivery method or system that can be employed in delivering an implant device to a target region.

As shown in FIG. 11A, the device 700 can be loaded onto the catheter 710 without having the device 700 and the catheter 710 or otherwise require the catheter 710 to be inserted into an inner volume of the device 700. As such, the device 700 can be carried on only a portion of the outer surface of the catheter 710. In the illustrated embodiment, the catheter 710 is shown as a hollow, tubular catheter; however, the catheter 710 can be replaced by a flat delivery substrate or solid core member whose size can be further decreased in order to access small vessels while providing a sufficiently rigid structure against which the device can be supported in a collapsed configuration. Sufficient rigidity is necessary in order to prevent the catheter or support device from bending in response to the bias force exerted by the link member(s) of the device.

According to various embodiments of the subject technology, the support frame may comprise at least one of stainless steel, nickel titanium (NiTi), cobalt chromium (CoCr), titanium, a polymer, a polyester based material, a tyrosine based polycarbonate, a polyethylene based material, Teflon (e.g., including expanded Teflon), and other suitable materials known to those of ordinary skill in the art. In some embodiments, the support frame may comprise at least one of polyethylene, polyglicolide, polylactide, c-caprolactone, polycarbonate, hydroxyalkanote, para dioxinine, polytetrafluoroethylene (PTFE), expanded polytetrafluoroethylene (ePTFE), PLA, PGA, PLLA, PDLLA, PDO, PCL, and other suitable materials known to those of ordinary skill in the art. In some embodiments, the support frame and/or occlusion membrane may comprise a bioabsorbable material, beneficially allowing for their controlled degradation. In some embodiments, the support frame and/or occlusion membrane may be formed of bioabsorbable material to have a controlled degradation anywhere between about 3 months to about 3 years depending on the desired application of support frame. In some embodiments, the controlled degradation may be less than about 3 months or greater than about 3 years. For example, hydrolysis of ester linkages or effects of enzymatic degradation may be utilized for the controlled degradation.

According to various embodiments of the subject technology, occlusion membrane may be used to occlude, partially or completely, luminal structure in which an implant is deployed. In some embodiments as used herein, occlusion may refer to either partial or complete occlusion. Some embodiments can be deployed in vessels having dimensions of between about 3 mm to about 20 mm. This exceptional and advantageous ability of embodiments of the medical implants disclosed herein to provide stenting in such small vessels is made possible, for example, due to the minimal delivery profile can be achieved using such embodiments. The target delivery profile can be about 8 Fr or smaller. Further, some embodiments can optionally comprise a fibrous membrane component, in various clinical applications, as discussed above. According to some embodiments, implants disclosed herein having a fibrous membrane feature can have an expanded diameter of between about 3 mm to about 22 mm.

According to various aspects of the subject technology, implants disclosed herein may be used for various applications for reducing or stopping flow through a luminal structure in a patient. Implants of the subject technology may be used for rapid, well-controlled, and reliable occlusion of luminal structures. For example, the luminal structure may comprise at least one of a blood vessel, a body organ, a lung, an airway, a Fallopian tube, a cervical canal, a vagina, a cervix, a vas deferens, a bronchus, a ureter, a colon, a rectum, an anus, a bio duct, a pancreatic duct, or other suitable tubular structures known to those of ordinary skill in the art. Some embodiments can be used to close a ductus arteriosis from a patent ductus arteriosis. In some embodiments, implants of the present disclosure may be used for temporary occlusion in cases of lung disease, or for temporary occlusion of female reproductive organs for contraceptive purposes. In some embodiments, implants of the present disclosure may be removed, or flow may be restored through the luminal structure to restore original organ functions.

In some embodiments, implants of the present disclosure may be used for various endoluminal occlusion procedures, including procedures for the lungs (e.g., selective endobronchial occlusion for lung reduction, occlusion of bronchopleural or bronchocutaneous fistulas, endovascular occlusion of pulmonary AVMs and fistulas or aortopulmonary anastomoses) and procedures for reproductive organs (e.g., endoluminal occlusion of vas deferens or Fallopian tubes for minimally-invasive contraceptive intervention, endovascular occlusion of varicocele in males and low abdominal gonadal veins for reducing or completely eliminating chronic pelvic pain syndrome in females). In some embodiments, implants of the present disclosure may be used for reducing or stopping blood loss from a damaged blood vessel, closing an abnormal blood vessel or a blood vessel supplying a vascular anomaly, or interrupting blood supply to an organ or part of an organ for permanent devascularization (e.g., closure of splenic artery in spleen laceration, devascularization of tissues involved by neoplastic process, either pre-operatively or as a palliative measure). In some embodiments, implants of the present disclosure may be used for various endovascular (e.g., neural and peripheral) procedures including procedures for giant cerebral and skull base aneurysms (ruptured and non-ruptured), head and neck arteriovenous fistulas, dissecting intracranial and extracranial vessels, traumatic and non-traumatic vessel injury or rupture (e.g., pelvic hemorrhages in trauma patients, carotid blow-out in patients with head and neck cancers, hemorrhage induced by a neoplasia, etc.), and devascularization prior to (or as an alternative to) surgical resection of various organs or tumors.

In certain embodiments, implants of the present disclosure may be used for various organs, including for example, the spleen (e.g., endovascular occlusion as a preoperative intervention or as an alternative to surgical resection with indications including traumatic hemorrhage, hypersplenism, bleeding secondary to portal hypertension or splenic vein thrombosis, and various disorders such as thalassemia major, thrombocytopenia, idiopathic thrombocytopenic purpura, Gaucher disease, and Hodgkin disease), the liver (e.g., occlusion of portal veins collaterals as adjunct to a transjugular intrahepatic portosystemic shunt (TIPS), occlusion of the TIPS itself in cases of encephalopathy, occlusion of intrahepatic arterioportal fistulas), the kidney (e.g., endoluminal ureteral occlusion for intractable lower urinary tract fistula with urine leakage, or for the treatment of uretero-arterial fistulae, endovascular occlusion as an alternative to surgical resection for end-stage renal disease or renovascular hypertension requiring unilateral or bilateral nephrectomy and renal transplant with native kidneys in situ), and the heart (e.g., occlusion of coronary arteriovenous fistulas, transarterial embolization of Blalock-Taussig shunts). The application of implants of the present disclosure is not limited to applications for human patients, but may also include veterinary applications.

According to some embodiments, covers (including patches) disclosed herein and in the above-noted patent applications, including but not limited to the cover 132, can be attached to a respective implant. Covers disclosed herein may be attached to one or both ends or an implant and/or a middle region of an implant.

According to various embodiments of the subject technology, covers may be used to occlude, partially or completely, luminal structure in which a respective implant is deployed. In some embodiments as used herein, occlusion may refer to either partial or complete occlusion. In some embodiments, covers include at least one of a polyurethane, a polyanhidrate, PTFE, ePTFE, silicone, and other suitable materials known to those of ordinary skill in the art. In some embodiments, covers may be elastic. In some embodiments, covers may be permeable or non-permeable.

In some embodiments, an average thickness of a cover is between about 0.0005 inches and about 0.006 inches. In some aspects, the average thickness of a cover may be less than about 0.0005 inches or greater than about 0.006 inches. In certain embodiments, an average thickness of a distal portion of a cover is greater than an average thickness of a proximal portion of a cover. Such a configuration may ensure that more flow may be reduced at the distal portion of a cover. In some embodiments, the average thickness of the distal portion of a cover is between about 0.002 inches and about 0.012 inches. In some embodiments, the average thickness of the distal portion of a cover may be less than about 0.002 inches or greater than about 0.012 inches. In some embodiments, the average thickness of the proximal portion of a cover is between about 0.0005 inches and about 0.006 inches. In some embodiments, the average thickness of the proximal portion of a cover may be less than about 0.0005 inches or greater than about 0.006 inches.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 55. The other clauses can be presented in a similar manner.

Clause 1. An expandable device for delivery to a target location in a body vessel, comprising: a frame comprising proximal and distal members and a link member having a first end coupled to the proximal member and a second end coupled to the distal member, the proximal and distal members being at opposite ends of a longitudinal axis; wherein the frame is expandable from (1) a collapsed configuration in which (i) a first plane passes through the proximal member and a second plane passes through the distal member, and (ii) the link member extends substantially parallel relative to the longitudinal axis, to (2) an expanded configuration, in moving to which (a) the first and second planes each move angularly, relative to the longitudinal axis, from the collapsed configuration by between about 10 degrees and about 170 degrees, and (b) the link member foreshortens along the longitudinal axis to bias the proximal member toward the distal member; and a cover member coupled to the frame.

Clause 2. The device of Clause 1, wherein at least one of the proximal or distal members comprises an annular shape.

Clause 3. The device of Clause 2, wherein the proximal and distal members each comprise an annular shape.

Clause 4. The device of any of Clauses 2-3, wherein, in the collapsed configuration, the annular shape is positioned in an oblong, deflected state.

Clause 5. The device of any of Clauses 2-4, wherein, in the expanded configuration, the annular shape is positioned in a substantially circular state.

Clause 6. The device of any of Clauses 2-5, wherein the annular shape has an expanded diameter of between about 5 mm and about 15 mm.

Clause 7. The device of Clause 6, wherein the annular shape has an expanded diameter of between about 7 mm and about 13 mm.

Clause 8. The device of Clause 7, wherein the annular shape has an expanded diameter of between about 8 mm and about 12 mm.

Clause 9. The device of any of Clauses 1-8, further comprising a second link member having a first end coupled to the proximal member and a second end coupled to the distal member.

Clause 10. The device of Clause 9, wherein the first and second link members extend in opposite directions about a periphery of the device.

Clause 11. The device of any of Clauses 9-10, wherein the first and second link members extend in opposite directions about a circumference of the device.

Clause 12. The device of any of Clauses 1-11, wherein, in the collapsed configuration, the first and second end sections of the proximal and distal members are positioned substantially parallel relative to the longitudinal axis.

Clause 13. The device of any of Clauses 1-12, wherein the proximal and distal members each comprise a midsection and opposing first and second end sections, and wherein the link member first end is coupled to the proximal member midsection and the link member second end is coupled to the distal member midsection.

Clause 14. The device of any of Clauses 1-13, wherein the proximal and distal members each comprise opposing first and second end sections separated by a midsection, the longitudinal axis passing through the midsection, and wherein, in the collapsed configuration, the first and second end sections of the proximal and distal members are spaced at a first distance from the longitudinal axis, and wherein, in the expanded configuration, the first and second sections of the proximal and distal members are spaced at a second distance from the longitudinal axis, the first distance being less than the second distance.

Clause 15. The device of Clause 14, wherein the link member first end is coupled to the proximal member midsection and the link member second end is coupled to the distal member midsection.

Clause 16. The device of any of Clauses 1-15, wherein, in the expanded configuration, at least one dimension of the proximal member expands within the first plane and at least one dimension of the distal member expands within the second plane.

Clause 17. The device of Clause 16, wherein the proximal and distal members comprise an annular shape, wherein, in the collapsed configuration, the proximal and distal members are positioned in a substantially oblong shape, and wherein, in the expanded configuration, the proximal and distal members are positioned in a substantially circular shape.

Clause 18. The device of any of Clauses 1-17, wherein, in the collapsed configuration, the first and second planes each are oriented at angles of between about 10° and about 50° relative to the longitudinal axis.

Clause 19. The device of any of Clauses 1-18, wherein, in the collapsed configuration, the first and second planes each are oriented at angles of between about 20° and about 40° relative to the longitudinal axis.

Clause 20. The device of any of Clauses 1-19, wherein, in the collapsed configuration, the first and second planes each are oriented at angles of between about 25° and about 35° relative to the longitudinal axis.

Clause 21. The device of any of Clauses 1-20, wherein, in the collapsed configuration, the first and second planes each are oriented at an angle of about 30° relative to the longitudinal axis.

Clause 22. The device of any of Clauses 1-21, wherein, in the expanded configuration, the first and second planes each are oriented at angles of between about 70° and about 110° relative to the longitudinal axis.

Clause 23. The device of any of Clauses 1-22, wherein, in the expanded configuration, the first and second planes each are oriented at angles of between about 80° and about 100° relative to the longitudinal axis.

Clause 24. The device of any of Clauses 1-23, wherein, in the expanded configuration, the first and second planes each are oriented at angles of between about 85° and about 95° relative to the longitudinal axis.

Clause 25. The device of any of Clauses 1-24, wherein, in the expanded configuration, the first and second planes each are oriented at an angle of about 90° relative to the longitudinal axis.

Clause 26. The device of any of Clauses 1-25, wherein, in the expanded configuration, the link member foreshortens by moving from a substantially linear configuration to an arcuate configuration.

Clause 27. The device of any of Clauses 1-26, wherein the link member is substantially helical shaped.

Clause 28. The device of any of Clauses 1-27, wherein the link member is substantially U-shaped.

Clause 29. The device of any of Clauses 1-28, wherein the device foreshortens by over 20% when expanding from the collapsed configuration to the expanded configuration.

Clause 30. The device of any of Clauses 1-29, wherein the device foreshortens by over 30% when expanding from the collapsed configuration to the expanded configuration.

Clause 31. The device of any of Clauses 1-30, wherein the device foreshortens by over 40% when expanding from the collapsed configuration to the expanded configuration.

Clause 32. The device of any of Clauses 1-31, wherein the device foreshortens by over 50% when expanding from the collapsed configuration to the expanded configuration.

Clause 33. The device of any of Clauses 1-32, wherein the device foreshortens by over 60% when expanding from the collapsed configuration to the expanded configuration.

Clause 34. The device of any of Clauses 1-33, wherein the device foreshortens by over 70% when expanding from the collapsed configuration to the expanded configuration.

Clause 35. The device of any of Clauses 1-34, wherein the device foreshortens by over 80% when expanding from the collapsed configuration to the expanded configuration.

Clause 36. An expandable device for delivery to a target location in a body vessel, comprising: a frame comprising proximal and distal annular members, a first link member being coupled to the proximal and distal annular members, and a second link member being coupled to the proximal and distal annular members, wherein the frame is expandable from (1) a collapsed configuration, in which (i) the proximal and distal annular members are compressed into an oblong shape and oriented substantially parallel or oblique relative to a longitudinal axis of the frame, and (ii) the first and second link members extend substantially parallel relative to the longitudinal axis, to (2) an expanded configuration, in which (a) the proximal and distal annular members are substantially circular and biased toward a substantially perpendicular orientation relative to the longitudinal axis, and (b) the first and second link members foreshorten along the longitudinal axis to bias the proximal annular member toward the distal annular member; and a cover member coupled to the frame.

Clause 37. The device of Clause 36, wherein, in the collapsed configuration, the first and second link members have a first longitudinal extent, and in the expanded configuration, the first and second link members have a second longitudinal extent, the second longitudinal extent being less than the first longitudinal extent.

Clause 38. The device of any of Clauses 36-37, wherein, in the collapsed configuration, the proximal annular member extends along the longitudinal axis at a first longitudinal extent that is greater than a cross-sectional dimension of the proximal annular member, and wherein, in the collapsed configuration, the distal annular member is extends along the longitudinal axis at a second longitudinal extent that is greater than a cross-sectional dimension of the distal annular member.

Clause 39. The device of any of Clauses 36-38, wherein, in the collapsed configuration, the proximal and distal annular members longitudinally overlap each other.

Clause 40. The device of any of Clauses 36-39, wherein the first and second link members each comprise an arcuate body, biased to a substantially linear shape in the collapsed configuration and to a bowed shape in the expanded configuration.

Clause 41. The device of any of Clauses 36-40, wherein the first and second link members comprise springs.

Clause 42. The device of any of Clauses 36-41, wherein, in the expanded configuration, the first and second link members are substantially V-shaped.

Clause 43. The device of any of Clauses 36-42, wherein, in the expanded configuration, the first and second link members are substantially U-shaped.

Clause 44. The device of any of Clauses 36-43, wherein the first link member is coupled to first sides of the proximal and distal annular members and the second link member is coupled to second sides, opposing the first sides, of the proximal and distal annular members.

Clause 45. The device of any of Clauses 36-44, wherein the device foreshortens by over 20% when expanding from the collapsed configuration to the expanded configuration.

Clause 46. The device of any of Clauses 36-45, wherein the device foreshortens by over 30% when expanding from the collapsed configuration to the expanded configuration.

Clause 47. The device of any of Clauses 36-46, wherein the device foreshortens by over 40% when expanding from the collapsed configuration to the expanded configuration.

Clause 48. The device of any of Clauses 36-47, wherein the device foreshortens by over 50% when expanding from the collapsed configuration to the expanded configuration.

Clause 49. The device of any of Clauses 36-48, wherein the device foreshortens by over 60% when expanding from the collapsed configuration to the expanded configuration.

Clause 50. The device of any of Clauses 36-49, wherein the device foreshortens by over 70% when expanding from the collapsed configuration to the expanded configuration.

Clause 51. The device of any of Clauses 36-50, wherein the device foreshortens by over 80% when expanding from the collapsed configuration to the expanded configuration.

Clause 52. The device of any of Clauses 36-51, further comprising an intermediate annular member coupled to the first and second link members intermediate the proximal and distal annular members.

Clause 53. The device of any of Clauses 36-52, the first and second link members are coupled to the proximal annular member at first and second coupling points and to the distal annular member at third and fourth coupling points, wherein the first and second coupling points are spaced further apart from the third and fourth coupling points in the collapsed configuration and in the expanded configuration.

Clause 54. The device of any of Clauses 36-53, wherein the proximal and distal annular members have expanded diameters of between about 5 mm and about 15 mm.

Clause 55. The device of Clause 54, wherein the proximal and distal annular members have expanded diameters of between about 7 mm and about 13 mm.

Clause 56. The device of Clause 55, wherein the proximal and distal annular members have expanded diameters of between about 8 mm and about 12 mm.

Clause 57. The device of any of Clauses 36-56, wherein the device has a longitudinal length in the expanded configuration of between about 3 mm and about 12 mm.

Clause 58. The device of Clause 57, wherein the device has a longitudinal length in the expanded configuration of between about 4 mm and about 10 mm.

Clause 59. The device of Clause 58, wherein the device has a longitudinal length in the expanded configuration of between about 5 mm and about 7 mm.

Clause 60. A delivery system for delivering an occlusive device to a target vessel, the system comprising: a handle portion; a tubular shaft comprising a proximal end, coupled to the handle portion, and a distal end, comprising a lumen; a delivery component slidably disposed within the lumen and configured to advance an occlusive device within the lumen for delivery to the target vessel; an actuation component coupled to the handle portion and the delivery component for selectively advancing or retracting the delivery component relative to the shaft; and a release member coupled to the delivery component, the release member being movable between an engaged position in which the release member engages the occlusive device relative to the delivery component, and a disengaged position, in which the occlusive device is disengaged from the delivery component.

Clause 61. The system of Clause 60, wherein the shaft comprises a needle having a beveled tip.

Clause 62. The system of any of Clauses 60-61, wherein the lumen is between about 3 Fr and about 9 Fr.

Clause 63. The system of Clause 62, wherein the lumen is between about 4 Fr and about 8 Fr.

Clause 64. The system of Clause 63, wherein the lumen is between about 5 Fr and about 7 Fr.

Clause 65. The system of any of Clauses 60-64, wherein the shaft has a length of between about 8 cm to about 15 cm.

Clause 66. The system of Clause 65, wherein the shaft has a length of between about 10 cm to about 12 cm.

Clause 67. The system of any of Clauses 60-67, wherein the delivery component is configured to support an occlusive device along an outer surface thereof.

Clause 68. The system of any of Clauses 60-68, wherein the delivery component comprises a hollow tubular member.

Clause 69. The system of any of Clauses 60-69, wherein the delivery component comprises an atraumatic tip.

Clause 70. The system of Clause 69, wherein the delivery component comprises a rounded tip.

Clause 71. The system of Clause 69, wherein the tip comprises a substantially rounded conical shape.

Clause 72. The system of any of Clauses 69-71, wherein the tip is configured to support the device thereon.

Clause 73. The system of any of Clauses 60-72, wherein the release member comprises a wire extending through a lumen of the delivery component, the wire configured to engage at least one portion of a device supported on the delivery component.

Clause 74. The system of Clause 73, wherein the wire engages the device in two locations along the delivery component.

Clause 75. The system of Clause 74, wherein the delivery component comprises proximal and distal slots into which first and second portions of the device can be coupled with the wire.

Clause 76. A method of implanting an occlusive device, comprising: advancing a needle subcutaneously and into a target vessel, the needle having a lumen in which an occlusion device is disposed, the device comprising any of the devices recited in Clauses 1 to 59; and advancing the device out of the lumen to release the device into the target vessel.

Clause 77. The method of Clause 76, wherein the advancing comprises advancing the needle into a perforator artery.

Clause 78. The method of Clause 77, wherein the perforator vessel extends between a deep vein and a superficial vein in a limb of a patient.

Clause 79. The method of any of Clauses 77-78, wherein the perforator vessel comprises a thigh perforator, a knee perforator, a leg perforator, an ankle perforator, or a foot perforator.

Clause 80. The method of any of Clauses 77-79, wherein the perforator vessel comprises one of a Hunterian perforator, a Dodd perforator, a Boyd perforator, a Cockett perforator, a fibular perforator.

Clause 81. The method of any of Clauses 77-80, wherein the perforator vessel has a length of less than 10 cm.

Clause 82. The method of any of Clauses 77-81, wherein the perforator vessel has a length of less than 7 cm.

Clause 83. The method of any of Clauses 77-82, wherein the perforator vessel has a length of less than 5 cm.

Clause 84. The method of any of Clauses 76-83, wherein the advancing comprises advancing a delivery component from within the needle to expose the device within the vessel.

Clause 85. The method of Clause 84, further comprising, after advancing the delivery component from within the needle, proximally retracting an actuation component relative to the delivery component to release the device.

Clause 86. The method of Clause 85, wherein the proximally retracting comprises sequentially disengaging first and second portions of the device.

Clause 87. A method of implanting an occlusive device in a perforator vessel, the method comprising: introducing a needle through skin of a patient; advancing the needle into a perforator vessel, the perforator vessel extending between a superficial vein and a deep vein; distally advancing a delivery component from within the needle until a distal end of the delivery component extends into the deep vein; releasing a distal portion of the occlusive device into the deep vein; proximally withdrawing the needle from the perforator vessel such that the device is exposed within the vessel; and releasing a proximal portion of the device into the superficial vein such that the device blocks flow through the vessel.

Clause 88. The method of Clause 87, wherein the releasing the distal portion comprises proximally retracting an actuation component relative to the delivery component to disengage the distal portion from the delivery component.

Clause 89. The method of any of Clauses 87-88, wherein the releasing the proximal portion comprises proximally retracting an actuation component relative to the delivery component to disengage the proximal portion from the delivery component.

Clause 90. The method of any of Clauses 87-89, wherein upon releasing the proximal portion, the device foreshortens within the perforator vessel.

Clause 91. The method of any of Clauses 87-90, wherein the advancing comprises guiding the needle using an imaging component.

Clause 92. The method of Clause 91, wherein the imaging component comprises a handheld ultrasound device Clause 93. The method of any of Clauses 87-92, wherein the introducing comprises introducing the needle through a from moral or jugular access point.

Further Considerations

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. A method of implanting an occlusive device in a perforator vessel, the method comprising:
    introducing a needle through skin of a patient;
    advancing the needle into a perforator vessel, the perforator vessel extending between a superficial vein and a deep vein;
    distally advancing a delivery component from within the needle until a distal end of the delivery component extends into the deep vein;
    releasing a distal portion of the occlusive device into the deep vein;
    proximally withdrawing the needle from the perforator vessel such that the device is exposed within the vessel; and
    releasing a proximal portion of the device into the superficial vein such that the device blocks flow through the vessel.

2. The method of claim 1, wherein the releasing the distal portion comprises proximally retracting an actuation component relative to the delivery component to disengage the distal portion from the delivery component.

3. The method of claim 1, wherein the releasing the proximal portion comprises proximally retracting an actuation component relative to the delivery component to disengage the proximal portion from the delivery component.

4. The method of claim 1, wherein upon releasing the proximal portion, the device foreshortens within the perforator vessel.

5. The method of claim 1, wherein the advancing the needle into the perforator vessel comprises guiding the needle using an imaging component.

6. The method of claim 5, wherein the imaging component comprises a handheld ultrasound device.

7. The method of claim 1, wherein the introducing comprises introducing the needle through a from moral or jugular access point.

8. The method of claim 1, wherein the perforator vessel comprises a thigh perforator, a knee perforator, a leg perforator, an ankle perforator, or a foot perforator.

9. The method of claim 1, wherein the perforator vessel comprises one of a Hunterian perforator, a Dodd perforator, a Boyd perforator, a Cockett perforator, a fibular perforator.

10. The method of claim 1, wherein the perforator vessel has a length of less than 10 cm.

11. A method of implanting an occlusive device, comprising:
    advancing a needle subcutaneously and into a target vessel extending between a superficial vein and a deep vein, the needle having a lumen in which the occlusion device is disposed, and advancing the occlusion device out of the lumen to release the device into the target vessel, the advancing the occlusion device out of the lumen comprising:
    advancing a catheter with the occlusion device supported thereon until a distal end of the catheter enters or is positioned adjacent the deep vein;
    releasing a distal portion of the occlusion device from engagement with the catheter;
    releasing and permitting a proximal end portion of the occlusion device to expand into the superficial vein; and
    proximally withdrawing the needle from the target vessel to expose the device within the target vessel.

12. The method of claim 11, wherein the target vessel comprises a perforator vessel.

13. The method of claim 12, wherein advancing the needle into the perforator vessel comprises advancing a guidewire into the perforator vessel to facilitate introduction of the needle into the perforator vessel.

14. The method of claim 12, wherein the perforator vessel comprises a thigh perforator, a knee perforator, a leg perforator, an ankle perforator, or a foot perforator.

15. The method of claim 12, wherein the perforator vessel comprises one of a Hunterian perforator, a Dodd perforator, a Boyd perforator, a Cockett perforator, a fibular perforator.

16. The method of claim 11, wherein the releasing the distal portion of the occlusion device comprises proximally retracting an actuation component relative to the catheter to disengage the distal portion from the catheter.

17. The method of claim 11, wherein the releasing the proximal end portion of the occlusion device comprises proximally retracting an actuation component relative to the catheter to disengage the proximal end portion from the catheter.

18. The method of claim 11, wherein upon releasing the proximal end portion, the device foreshortens within the target vessel.

19. The method of claim 11, wherein the advancing the needle subcutaneously and into the target vessel comprises guiding the needle using an imaging component.

20. The method of claim 19, wherein the imaging component comprises a handheld ultrasound device.

\* \* \* \* \*